US011238967B1

(12) United States Patent
Bayuzick et al.

(10) Patent No.: US 11,238,967 B1
(45) Date of Patent: Feb. 1, 2022

(54) SYSTEMS AND METHODS FOR GENERATING DYNAMIC GRAPHICAL USER INTERFACES FOR DOSE RECALCULATIONS AND ADJUSTMENTS

(71) Applicant: Flatiron Health, Inc., New York, NY (US)

(72) Inventors: Henry Bayuzick, Boston, MA (US); Kimberly Wiederkehr, Brooklyn, NY (US); Haley Spitz, New York, NY (US); Nathaniel J. Wade, Rochester, NY (US); Alison Fugaro, Atlanta, GA (US); Lauren Urke, Medina, MN (US); Patrick Hempton, Austin, TX (US); Harry Lee, Brooklyn, NY (US); Kalpana Natarajan, Fremont, CA (US); Emily Ling, San Jose, CA (US); Michael Troughton, New York, NY (US)

(73) Assignee: FLATIRON HEALTH, INC., New York, NY (US)

(*) Notice: Subject to any disclaimer, the term of this patent is extended or adjusted under 35 U.S.C. 154(b) by 0 days.

(21) Appl. No.: 17/184,112

(22) Filed: Feb. 24, 2021

(51) Int. Cl.
G06F 3/0481 (2013.01)
G16H 20/10 (2018.01)
G16H 10/60 (2018.01)
G06F 3/0482 (2013.01)

(52) U.S. Cl.
CPC .......... *G16H 20/10* (2018.01); *G06F 3/0482* (2013.01); *G06F 3/04817* (2013.01); *G16H 10/60* (2018.01)

(58) Field of Classification Search
CPC combination set(s) only.
See application file for complete search history.

(56) References Cited

U.S. PATENT DOCUMENTS

| 8,224,667 | B1* | 7/2012 | Miller | G16H 20/10 705/2 |
| 2008/0015549 | A1* | 1/2008 | Maughan | G06F 19/00 604/890.1 |
| 2008/0097792 | A1* | 4/2008 | Marge | G16H 20/10 705/3 |
| 2009/0106313 | A1* | 4/2009 | Boldyga | G16H 20/10 |

(Continued)

*Primary Examiner* — Hien L Duong
(74) *Attorney, Agent, or Firm* — Finnegan, Henderson, Farabow, Garrett & Dunner LLP

(57) ABSTRACT

A system for generating dynamic multi-layered graphical user interfaces may include at least one processing device configured to retrieve treatment regimen data for a patient from at least one networked database, retrieve patient attribute data for the patient, generate a graphical user interface reflecting a medication identified in the treatment regimen data and one or more associated patient attributes, compare the extracted patient attributes to one or more thresholds in a rule set, the rule set correlating a dose of the medication to one or more expected values of the extracted patient attributes, evaluating at least one condition of at least rule in the rule set, generate, based on the evaluation an interactive icon for display in the graphical user interface, and generate an overlay window displayed adjacent the interactive icon, the overlay window providing details associated with the interactive icon.

20 Claims, 23 Drawing Sheets

(56) References Cited

U.S. PATENT DOCUMENTS

| | | | | |
|---|---|---|---|---|
| 2011/0313789 | A1* | 12/2011 | Kamen | G16H 20/10 |
| | | | | 705/3 |
| 2016/0314251 | A1* | 10/2016 | Pratsevall | A61B 5/4839 |
| 2017/0043089 | A1* | 2/2017 | Handler | H04L 67/12 |
| 2019/0326002 | A1* | 10/2019 | Mould | A61B 5/4836 |
| 2020/0176093 | A1* | 6/2020 | Kuchibotla | G16H 15/00 |
| 2020/0219605 | A1* | 7/2020 | Govindjee | G16H 40/67 |
| 2020/0321096 | A1* | 10/2020 | Mould | G16H 50/50 |

* cited by examiner

| 300 | | | | 🏠 Los Altos Office ▾ | ☺ | | Caregiver1 ▾ | ⬈ Log out | |
|---|---|---|---|---|---|---|---|---|---|

| Inbox ⬆ | Patient1 | 302 |
| Search 🔍 | Room: None ▾ Sex: F MRN: 1234567 DOB: 12/20/1965 (55) MD: Caregiver1 | |

GENERAL
Visit lists
Scheduler
Reports
New task
New task
Insurance Auth

PATIENT CHART
Write Script
Demographics
Summary
Documents
Treatment plan
Orders
Visit notes
Referrals
Text note
Care plan
Research

LABS & Vitals
Collection record
Lab results
Vitals signs

NURSE
MAR
Superbill

Orders for 11/23/2020 [Prev] [Next] [Today] 📅 [CCD for 11/2/2020] 📅 Summary: [XML] [HTML]

[Back to Treatment Plan] [Print] [Goto MAR/Nurse Note] [Approve All] [Change Hx] Patient Education ☑ Show medication-specific patent-education icons

New: Drug, Test, Radiology, Activity, Multiple Orders, Orderset    BSA: 1.64 (last wt on 10/27/2020) SrCr: 1 mg/dL (10/27/2020)
     CrCl: 54.59 mL/min
Actions: Delay/Move, Delete, Print Labels, Cancel    Wt: 120 lb (54.4 kg) Ht: 68 in (172.7 cm)
Diagnoses: 9/21/2020 Primary 174.1/C50.112 Malignant neoplasm of central portion of left female breast
Allergies:
Regimens: 1) AC (DOXOrubicin 60 mg/m2 / Cyclophosphamide 600 mg/m2) q 21 days x 4 cycles
         Followed by DOCEtaxel (100mg/m2) Q 21 days X 4 (4:1)

⚠ Recalculate to ensure safe doses.
  The vitals and labs used to calculate 2 medications have changed significantly since they were last calculated.   ✕ — 308

[Adjust 2 doses] [Recalculate 2 doses] — 309

| Medication | Regimen dose | Adjusted dose | Vitals and labs used | Dose to be given | Last updated | Reason | Approve All |
|---|---|---|---|---|---|---|---|
| ⊟ Cycle 3, Day 1 - AC (DOXOrubicin 60 mg/m2 / Cyclophosphamide 60 mg/m2) q 21 days x 4 cycles Followed by DOCEtaxel (100 mg/m2) Q 21 days X 4 | | | | | | | |
| ☐ Palonosetron (Aloxi) ⓘ IVP | 250 mcg | None | NA | 250 mcg 📅 | Sep. 22, 2020 by Caregiver1 | No data | Planned |
| ☑ Doxorubicin ⓘ (Adriamycin) IVP 60/m2 | 60 mg/m² | 47.4 mg/m² (-21%) | ⚠ Latest bsa changed | ⚠ 108 mg -- Dose based on old value [Rounded] | Nov. 2, 2020 by Caregiver1 | Recalculated using latest vitals and labs | Planned |
| ☑ Cyclophosphamide ⓘ (Cytoxan) 600/m2 IV | 600 mg/m² | 477.9 mg/m² (-20.35%) | ⚠ Latest bsa changed | ⚠ 1086 mg - Dose based on old value [Rounded] | Nov. 2, 2020 by Caregiver1 | Recalculated using latest vitals and labs | Planned |

| Tests | Specimen | Instructions | Approval All |
|---|---|---|---|
| CBC | No need to fast | | Planned |
| CMP | Non Fast | | Planned |

FIG. 3A

Recalculate doses for 2 drugs 310

Patient1 F - #1234567 12/20/1965 (55)

| Medication | Regimen dose | Adjustment | Vitals and labs used | Dose to be given | |
|---|---|---|---|---|---|
| Cycle 4, Day 1 - AC (DOXOrubicin 60 mg/m2 / Cyclophosphamide 600 mg/m2) q 21 days x 4 cycles Followed by DOCEtaxel (100mg/m2) Q 21 days X 4 | | | | | |
| Doxorubicin (Adriamycin) IVP 60/m2 | 60 mg/m² | None | 1.81 m² → 1.65 m² | 108 mg [Rounded] | → 100 mg [Rounded] |
| Cyclophosphamide (Cytoxan) 600/m2 IV | 600 mg/m² | None | 1.81 m² → 1.65 m² | 1086 mg | → 990 mg |

Reason * —— 316          314        312

( ● ) Recalculated using latest vitals and labs ( ○ ) Other

Apply changes to * —— 318

( ○ ) This day only ( ○ ) All days (with a value) in the future          320

[ Cancel ]  [ Apply changes ]

FIG. 3B

Recalculate doses for 2 drugs

Patient1 F - #1234567 12/20/1965 (55)

| Medication | Regimen dose | Adjustment | Vitals and labs used | Dose to be given | |
|---|---|---|---|---|---|
| Cycle 4, Day 1 - AC (DOXOrubicin 60 mg/m2 / Cyclophosphamide 600 mg/m2) q 21 days x 4 cycles Followed by DOCEtaxel (100mg/m2) Q 21 days X 4 | | | | | |
| Doxorubicin (Adriamycin) IVP 60/m2 | 60 mg/m² | None | 1.81 m² → 1.65 m² | 108 mg [Rounded] | → 100 mg [Rounded] |
| Cyclophosphamide (Cytoxan) 600/m2 IV | 600 mg/m² | None | 1.81 m² → 1.65 m² | 1086 mg | → 990 mg |

Reason *

- ◉ Recalculated using latest vitals and labs
- ○ Other

Apply changes to *

- ○ This day only
- ◉ All days (with a value) in the future          322

⚠ Warning! Any future orders that have been approved will require additional approval

[ Cancel ]  [ Apply changes ]

FIG. 3C

| 400 | | 🏠 Los Altos Office ▾ | ⊙ | Caregiver1 ▾ | ⎋ Log out |
|---|---|---|---|---|---|
| Inbox 📥 | Patient1 Room: None, Sex: F MRN: 1234567 DOB: 12/20/1965 (55) MD: Caregiver1 Primary Insurance: None Phone number: Unknown ||||||
| Search 🔍 ||||||

GENERAL
Visit lists
Scheduler
Reports
New task
New task
Insurance Auth

PATIENT CHART
Write Script
Demographics
Summary
Documents  406
Treatment plan
Orders
Visit notes
Referrals  404
Text note
Care plan
Research

LABS & Vitals
Collection record
Lab results
Vitals signs

NURSE
MAR
Superbill

Orders for 11/23/2020  [Prev] [Next] [Today] 📅 [CCD for 11/2/2020] 📅   Summary: [XML] [HTML]

[Back to Treatment Plan] [Print] [Goto MAR/Nurse Note] [Approve All] [Change Hx]  Patient Education  ☑ Show medication-specific patent-education icons

New: Drug, Test, Radiology, Activity, Multiple Orders, Orderset   BSA: 1.64 (last wt on 10/27/2020) SrCr: 1 mg/dL (10/27/2020)
CrCl: 54.59 mL/min
Actions: Delay/Move, Delete, Print Labels, Cancel   Wt: 120 lb (54.4 kg) Ht: 68 in (172.7 cm)
Diagnoses: 9/21/2020 Primary 174.1/C50.112 Malignant neoplasm of central portion of left female breast
Allergies:
Regimens: 1) AC (DOXOrubicin 60 mg/m2 / Cyclophosphamide 600 mg/m2) q 21 days x 4 cycles
    410      Followed by DOCEtaxel (100mg/m2) Q 21 days X 4 (4:1)

[Adjust doses]   [Recalculate doses]  ⟵ 408

| ☐ Medication | Regimen dose | Adjusted dose | Vitals and labs used | Dose to be given | Last updated | Reason | Approve All |
|---|---|---|---|---|---|---|---|
| ☐ Cycle 4, Day 1 - AC (DOXOrubicin 60 mg/m2 / Cyclophosphamide 600 mg/m2) q 21 days x 4 cycles Followed by DOCEtaxel (100 mg/m2) Q 21 days X 4 ||||||||
| ☐ Palonosetron (Aloxi) ⓘ IVP | 250 mcg | None | NA | 250 mcg | Sep. 22, 2020 by Caregiver1 | No data | Planned |
| ☐ Doxorubicin ⓘ (Adriamycin) IVP 60/m2 | 60 mg/m² | None | 1.64 m² | 100 mg [Rounded]  402 | Nov. 2, 2020 by Caregiver1 | Recalculated using latest vitals and labs | Planned |
| ☐ Cyclophosphamide ⓘ (Cytoxan) 600/m2 IV | 600 mg/m² | None | 1.64 m² | 990 mg | Nov. 2, 2020 by Caregiver1 | Recalculated using latest vitals and labs | Planned |

| Tests | Specimen | Instructions | Approval All |
|---|---|---|---|
| CBC | | No need to fast | Planned |
| CMP | | Non Fast | Planned |

| Workflow | Value | Instructions | Approval All |
|---|---|---|---|
| CL2 | * | | Planned |

FIG. 4A

| | Los Altos Office ▼ | Caregiver1 ▼ | Log out |

| Inbox | Patient1 |
| Search | Room: None, Sex: F MRN: 1234567 DOB: 12/20/1965 (55) MD: Caregiver1 |
| | Primary Insurance: None Phone number: Unknown |

GENERAL
Visit lists
Scheduler
Reports
New task
New task
Insurance Auth

PATIENT CHART
Write Script
Demographics
Summary
Documents
Treatment plan
Orders
Visit notes
Referrals
Text note
Care plan
Research

LABS & Vitals
Collection record
Lab results
Vitals signs

NURSE
MAR
Superbill

Orders for 11/23/2020 [Prev] [Next] [Today] 📅 [CCD for 11/2/2020] 📅  Summary: [XML] [HTML]

[Back to Treatment Plan] [Print] [Goto MAR/Nurse Note] [Approve All] [Change Hx] Patient ☑ Show medication-specific
Education patent-education icons New: Drug, Test, Radiology, Activity, Multiple Orders, Orderset  BSA: 1.64 (last wt on 10/27/2020) SrCr: 1 mg/dL (10/27/2020)
CrCl: 54.59 mL/min
Actions: Delay/Move, Delete, Print Labels, Cancel  Wt: 120 lb (54.4 kg) Ht: 68 in (172.7 cm)
Diagnoses: 9/21/2020 Primary 174.1/C50.112 Malignant neoplasm of central portion of left female breast
Allergies:
Regimens: 1) AC (DOXOrubicin 60 mg/m2 / Cyclophosphamide 600 mg/m2) q 21 days x 4 cycles
412   Followed by DOCEtaxel (100mg/m2) Q 21 days X 4 (4:1)
[Adjust 2 doses] [Recalculate 2 doses] ⟵ 414

| Medication | Regimen dose | Adjusted dose | Vitals and labs used | Dose to be given | Last updated | Reason | Approve All |
|---|---|---|---|---|---|---|---|
| Cycle 4, Day 1 - AC (DOXOrubicin 60 mg/m2 / Cyclophosphamide 600 mg/m2) q 21 days x 4 cycles Followed by DOCEtaxel (100 mg/m2) Q 21 days X 4 | | | | | | | |
| ☐ Palonosetron (Aloxi) ⓘ IVP | 250 mcg | None | NA | 250 mcg | Sep. 22, 2020 by Caregiver1 | No data | Planned |
| ☑ Doxorubicin (Adriamycin) IVP 60/m2 ⓘ | 60 mg/m² | None | 1.64 m² | 100 mg [Rounded] | Nov. 2, 2020 by Caregiver1 | Recalculated using latest vitals and labs | Planned |
| ☑ Cyclophosphamide (Cytoxan) 600/m2 IV ⓘ | 600 mg/m² | None | 1.64 m² | 990 mg | Nov. 2, 2020 by Caregiver1 | Recalculated using latest vitals and labs | Planned |

| Tests | Specimen | Instructions | | | | | Approval All |
|---|---|---|---|---|---|---|---|
| CBC | | No need to fast | | | | | Planned |
| CMP | | Non Fast | | | | | Planned |

| Workflow | Value | Instructions | | | | | Approval All |
|---|---|---|---|---|---|---|---|
| CL2 | * | | | | | | Planned |

FIG. 4B

Adjust doses for 2 drugs

Patient1 F - #1234567 12/20/1965 (55)    418

Reduce all medication by

[ % of regimen dose ] [ Reduce ]

| Medication | Regimen dose | Adjustment | Dose to be given |
|---|---|---|---|
| Cycle 4, Day 1 - AC (DOXOrubicin 60 mg/m2 / Cyclophosphamide 600 mg/m2) q 21 days x 4 cycles Followed by DOCEtaxel (100mg/m2) Q 21 days X 4 | | | |
| Doxorubicin (Adriamycin) IVP 60/m2 | 60 mg/m² | ~~100%~~ → [100 % of regimen dose] <br> ~~60 mg/m²~~ → [60 mg/m2] | ~~100 mg~~ → [99 mg] Rounded <br> → 100 mg Rounded |
| Cyclophosphamide (Cytoxan) 600/m2 IV | 600 mg/m² | ~~100%~~ → [100 % of regimen dose] <br> ~~600 mg/m²~~ → [600 mg/m2] | ~~990 mg~~ → [990 mg] |

**Reason * ──416**

○ Thrombocytopenia    ○ Neutropenia
○ Gastrointestinal AE    ○ Peripheral Nervous System AE
○ Dosing protocol    ○ Other

Apply changes to *

○ This day only

○ All days (with a value) in the future

[ Cancel ] [ Apply changes ]

Adjust doses for 2 drugs

Patient1 F - #1234567 12/20/1965 (55)

Reduce all medication by

[ % of regimen dose ] [ Reduce ]

| Medication | Regimen dose | Adjustment | Dose to be given |
|---|---|---|---|
| Cycle 4, Day 1 - AC (DOXOrubicin 60 mg/m2 / Cyclophosphamide 600 mg/m2) q 21 days x 4 cycles Followed by DOCEtaxel (100mg/m2) Q 21 days X 4 | | | |
| Doxorubicin (Adriamycin) IVP 60/m2 | 60 mg/m² | ~~100%~~ → [ 80 ] % of regimen dose<br>~~60 mg/m²~~ → [ 48 ] mg/m2 | ~~100 mg~~ → [ 78.7 mg ] [Rounded]<br>→ 78 mg [Rounded] |
| Cyclophosphamide (Cytoxan) 600/m2 IV | 600 mg/m² | ~~100%~~ → [ 70 ] % of regimen dose<br>~~600 mg/m²~~ → [ 420 ] mg/m2 | ~~990 mg~~ → [ 688.8 mg ] → 689 mg [Rounded] |

Reason *    424          426

- ○ Thrombocytopenia     ○ Neutropenia
- ○ Gastrointestinal AE     ○ Peripheral Nervous System AE
- ○ Dosing protocol     ○ Other

Apply changes to *

- ○ This day only
- ○ All days (with a value) in the future

[ Cancel ] [ Apply changes ]

| 440 | | 🏠 Los Altos Office ▼ | 👤 | Caregiver1 ▼ | 🚪 Log out |

| Inbox 📥 | Patient1 |
| Search 🔍 | Room: None, Sex: F MRN: 1234567 DOB: 12/20/1965 (55) MD: Caregiver1 |
| | Primary Insurance: None Phone number: Unknown |

GENERAL
Visit lists
Scheduler
Reports
New task
New task
Insurance Auth

PATIENT CHART
Write Script 📝
Demographics
Summary
Documents
Treatment plan
Orders
Visit notes
Referrals
Text note
Care plan
Research

LABS & Vitals
Collection record
Lab results
Vitals signs

NURSE
MAR
Superbill

Orders for 11/23/2020 [Prev] [Next] [Today] 📅 [CCD for 11/2/2020] 📅   Summary: [XML] [HTML]

[Back to Treatment Plan] [Print] [Goto MAR/Nurse Note] [Approve All] [Change Hx] Patient ☑ Show medication-specific
Education patient-education icons
New: Drug, Test, Radiology, Activity, Multiple Orders, Orderset   BSA: 1.64 (last wt on 10/27/2020) SrCr: 1 mg/dL (10/27/2020)
CrCl: 54.59 mL/min
Actions: Delay/Move, Delete, Print Labels, Cancel   Wt: 120 lb (54.4 kg) Ht: 68 in (172.7 cm)
Diagnoses: 9/21/2020 Primary 174.1/C50.112 Malignant neoplasm of central portion of left female breast
Allergies:
Regimens: 1) AC (DOXOrubicin 60 mg/m2 / Cyclophosphamide 600 mg/m2) q 21 days x 4 cycles
Followed by DOCEtaxel (100mg/m2) Q 21 days X 4 (4:1)

[Adjust doses] [Recalculate doses]

| ☐ Medication | Regimen dose | Adjusted dose | Vitals and labs used | Dose to be given | Last updated | Reason | Approve All |
|---|---|---|---|---|---|---|---|
| ☐ Cycle 4, Day 1 - AC (DOXOrubicin 60 mg/m2 / Cyclophosphamide 600 mg/m2) q 21 days x 4 cycles Followed by DOCEtaxel (100 mg/m2) Q 21 days X 4 | | | | | | | |
| ☐ Palonosetron (Aloxi) ⓘ IVP | 250 mcg | None | NA | 250 mcg | Sep. 22, 2020 by Caregiver1 | No data | Planned |
| ☐ Doxorubicin (Adriamycin) IVP 60/m2 ⓘ | 60 mg/m² | 48 mg/m² (-20%) | 1.64 m² | 80 mg [Rounded] | Nov. 2, 2020 by Caregiver1 | Dosing Protocol | Planned |
| ☐ Cyclophosphamide (Cytoxan) 600/m2 IV ⓘ | 600 mg/m² | 420 mg/m² (-30%) | 1.64 m² | 693 mg | Nov. 2, 2020 by Caregiver1 | Dosing Protocol | Planned |

| Tests | Specimen | Instructions | Approval All |
|---|---|---|---|
| CBC | | No need to fast | Planned |
| CMP | | Non Fast | Planned |

| Workflow | Value | Instructions | Approval All |
|---|---|---|---|
| CL2 | * | | Planned |

FIG. 4H

| | Home  Group Inboxes | 🏠 Los Altos Office ▾   ⊙   Caregiver1 ▾   ⎋ Log out |
|---|---|---|

| Inbox 📥 | Patient1 |
|---|---|
| Search 🔍 | Room: None ▾  Sex: F  MRN: 1234567  DOB: 12/20/1965 (55)  MD: Caregiver1 |
| | Primary Insurance: Aetna  Phone number: (650) 123-2457  Memo: Co-pay $30 ✎ |

GENERAL
Visit lists
Scheduler
Reports
New task
Insurance Auth

PATIENT CHART
InHouseRX
Demographics
Summary
Documents
Treatment plan
Orders
Visit notes
Referrals
Text note
Care plan
Research

LABS & Vitals
Collection record
Lab results
Vitals signs

NURSE
MAR
Superbill

Billing
Financials

MAR/Nurse Note for 9/2/2020  Patient List  [Prev]  [Next]  [Today]  📅

[Save]  [Sign]  [Print]  [Goto Order]  [Goto Superbill]         [Refresh]  [Delete]

Business office must be set to "APPROVED" before delivering treatment.    [Go to Business Office]

One or more of the orders have not been approved.    [Review/approve]

This MAR/Nurse Note supersedes a previous one.    [Go to previous MAR]

Allergies: No Know Drug Allergies
Questionnaire (Is the patient experiencing any of the following?): Show
Venous Access documentation: Show
Regimens: 1) ABCD_xxxxxx: CiSplatin(75)D1-PEMExtrexed(500)D1-Pembrolizumab(200)D1 Q21D x 4-6 (4:1)      1102
MARS  New Medication  Copy Planned to Actual  Change Sequence  Patient Education ⚠ Recalculate to ensure safe doses.
   The vitals and labs used to calculate 1 medication has changed significantly since it was last calculate.   [Go to Orders]
   Change the dose on the Orders page

| Bag or Route | Drug | Planned | Actual | Waste | Fluid | Start | Stop | Duration Plan/Act | Dose Checks [All] |
|---|---|---|---|---|---|---|---|---|---|
| IM | Cyanocobatamin (Vitamin-B-12)Inj ⓘ | 1,000 mcg | --Not Approved-- | | | | | 0 | |
| IV | Pembrolizumab (Keytruda) ⓘ | 200mg | --Not Approved-- | | | | | 30 | |
| IV | CiSplatin ⓘ | 137mg | --Not Approved-- | | | | | 60 | |

Prescriptions

| Ordered Drug | Dose | Prescribed Drug | Quantity | Script Date |
|---|---|---|---|---|
| Dexamethasone oral (Decadron, DexPak) | 4mg | --Prescription Not Found-- | --Not Approved-- | |
| Folic Acid | 400mcg | --Prescription Not Found-- | --Not Approved-- | |

De-Access documentation: Show
Comments/Additional Information: Hide

FIG. 11

SYSTEMS AND METHODS FOR GENERATING DYNAMIC GRAPHICAL USER INTERFACES FOR DOSE RECALCULATIONS AND ADJUSTMENTS

BACKGROUND

Technical Field

The present disclosure relates to systems and methods for generating dynamic multi-layered dose recalculation and adjustment graphical user interfaces, and real-time alerts.

Background Information

Medical treatments typically involve a regimen of medication and/or therapy. Successful treatment regimens require careful calculation of the medication and therapy amounts, to ensure the safety of the patient and efficacy of the treatment. Such calculations account for vital signs and/or attributes (e.g., weight) of the patient so that the treatment is tailored to the patient. Treatment regimens spanning over a time period may require periodic changes to the medication or therapy amounts, as the patient's body changes due to illness, recovery, or side effects of the treatment regimen itself. For these reasons, it is important that caregivers monitor patient attributes throughout a treatment regimen and adjust treatment parameters as needed.

As an example, cancer patients often undergo one or more cycles of chemotherapy treatment, during which a combination of different drugs are administered to the patient in doses spread over the course of each cycle. Some chemotherapy drugs are administered in doses sized according to the patient's attributes such as body size, weight, or body surface area. Other drugs may be administered in doses based on the patient's lab test results for levels of various substances in the patient's blood or urine tests, such as, for example, serum creatinine levels in a tested blood sample. During the course of the chemotherapy regimen, the patient's weight is remeasured, and additional lab tests are conducted. Weight loss is a common side effect of chemotherapy, and therefore the patient's weight may drop significantly during the course of treatment and require a recalculation of chemotherapy drug dosages. Likewise, lab results may change over the weeks of chemotherapy, requiring drug dosage recalculation.

Computer systems have been used in recent years to record patient information. Computerized electronic health record (EHR) systems are typically used for tracking information about a patient and for providing status information about the patient's treatment regimen. As an example, EHRs can allow a caregiver to record lab results and measurements for a patient, request medications for the patient, and track medication doses that have been administered to the patient. Due to the plethora of information collected for each patient, some EHRs have cluttered user interfaces that present as much data as will fit on the display. These cluttered interfaces are often confusing or overwhelming to a caregiver user, or may cause the caregiver to overlook important changes in certain metrics. Other EHRs can provide user interfaces that are overly minimalistic, providing insufficient information on screen for the caregiver to fully understand the patient's current situation. Such user interfaces may require caregivers to access other user interfaces on different screens, different applications, or even other computer systems in order to gather additional information about the patient or to understand the context of the information shown, thereby tying up computer resources for generating and displaying the additional user interfaces, or requiring additional computer systems to provide caregivers with all necessary information. Moreover, the caregiver user's experience is marred by a need to navigate to other interfaces or computer systems, or a need for the caregiver to investigate the criteria used to determine patient metrics displayed on the interface.

In view of the drawbacks and deficiencies discussed of prior systems discussed above, improved caregiver computer systems and techniques are needed.

SUMMARY

Embodiments consistent with the present disclosure include systems and methods for generating dynamic graphical user interfaces for dose recalculation. Disclosed embodiments also provide improved graphical user interfaces for administering a treatment regimen using interactive multi-layer graphical user interfaces. The disclosed embodiments may be applicable to a wide range of patient treatment regimens, and may provide particular advantages and improvements in the treatment of cancer patients.

In one embodiment, a system is provided for generating dynamic multi-layered graphical user interfaces. The system may comprise a memory storing instructions, and at least one processor, the at least one processor being configured to execute the stored instructions. The at least one processor may be configured to perform operations including: retrieving, from at least one networked database, treatment regimen data for a patient; retrieving, from the at least one networked database, patient attribute data for the patient; generating a graphical user interface reflecting a medication identified in the treatment regimen data and one or more associated patient attributes, wherein the associated patent attributes are extracted from the patient attribute data; comparing the extracted patient attributes to one or more thresholds in a rule set, the rule set correlating a dose of the medication to one or more expected values of the extracted patient attributes; based on the comparison, evaluating at least one condition of at least one rule in the rule set; based on the evaluation, generating an interactive icon for display in the graphical user interface; and responsive to a selection of the interactive icon, generating an overlay window displayed adjacent the interactive icon, the overlay window providing details associated with the interactive icon.

In one embodiment, a method is provided for generating dynamic multi-layered graphical user interfaces. The method may be performed using at least one processor. The method may comprise: retrieving, by the at least one processor from at least one networked database, treatment regimen data for a patient; retrieving, by the at least one processor from the at least one networked database, patient attribute data for the patient; generating, by the at least one processor, a graphical user interface reflecting a medication identified in the treatment regimen data and one or more associated patient attributes, wherein the associated patent attributes are extracted from the patient attribute data; comparing, by the at least one processor, the extracted patient attributes to one or more thresholds in a rule set, the rule set correlating a dose of the medication to one or more expected values of the extracted patient attributes; evaluating, by the at least one processor based on the comparison, at least one condition of at least one rule in the rule set; generating, by the at least one processor based on the evaluation, an interactive icon for display in the graphical user interface; and generating, by the at least one processor responsive to a selection of the interactive icon, an overlay window displayed adjacent the interactive icon, the overlay window providing details associated with the interactive icon.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIGS. 3A-3E are illustrations of exemplary GUIs for dose recalculations and alerts, consistent with the present disclosure.

FIGS. 4A-4H are illustrations of exemplary GUIs for dose adjustments, consistent with the present disclosure.

FIG. 11 is an illustration of an exemplary GUI for providing alerts in a MAR page, consistent with the present disclosure.

DETAILED DESCRIPTION

Figure 1:
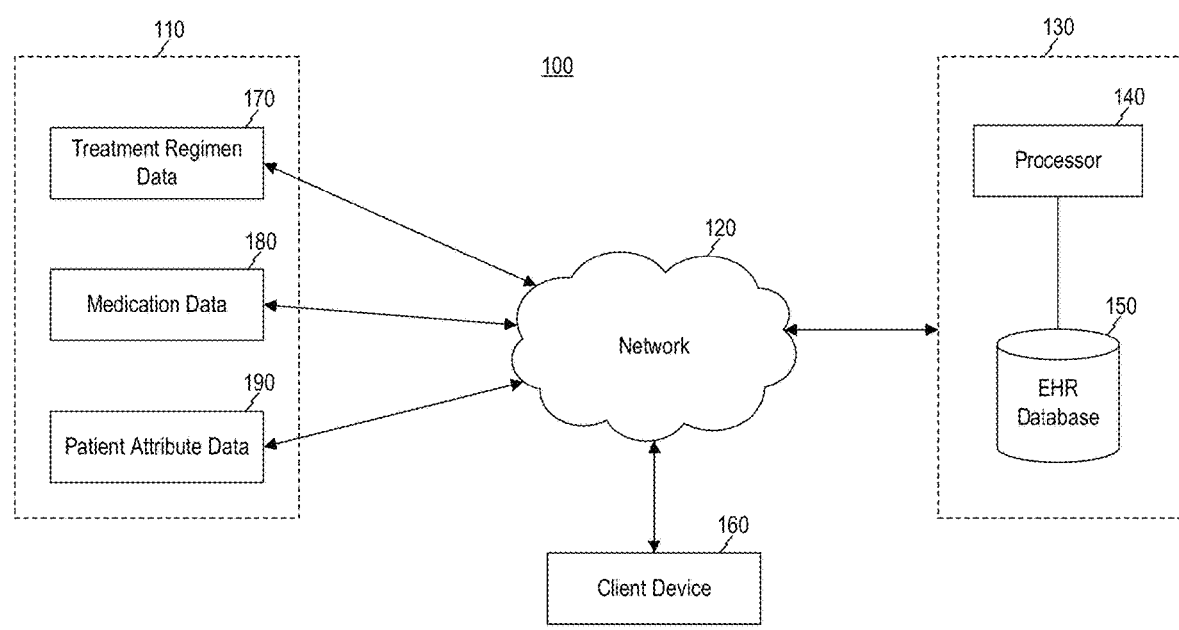
FIG. 1 is a block diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

The present disclosure provides systems and methods that may dynamically alert a user to recalculate dose calculations in a treatment regimen and generate updated and interactive graphical user interfaces for providing dose recalculation and adjustment information to a user. Dose recalculation alerts may be sent in real time as the system receives updated information about a patient, either through updated medical records, sensor devices, or input by a user into a computer terminal. In addition, a caregiver may be alerted to recalculate a dose based on passage of a predefined amount of time since last calculation, stage of treatment or other predefined event. After doses for medication or therapy are recalculated or adjusted, the system may generate one or more graphical user interfaces for providing the updated dose calculation with notations to alert a user to the change, and one or more layered graphical elements may be displayed based on a user's interactions with the interface. The layered graphical elements may provide, among other things, additional context about the dose changes, additional information explaining how the system calculated the change(s), or more detailed information about alerts for the user's attention. Through the implementation of one or more of these features, the disclosed embodiments may improve the user's experience by removing the need for the user to navigate to multiple different interfaces or computer applications to find information they need to understand the patient's dose calculation.

The disclosed embodiments also eliminate the need for a user to access different computer systems to find additional information about the dose calculation. The disclosed embodiments provide a graphical user interface that is intuitive, interactive, and provides selective amounts of information in a streamlined interface with dynamic overlay windows displayed as a layer over a main application interface window, allowing the user to instantly find additional information if necessary, while reducing clutter and unnecessary information on the base-level interface. These improvements can yield multiple enhancements to the associated computer systems, including reducing the computer resources necessary to generate the streamlined interface as compared to an interface filled with as much information as will fit the display. This consolidated and integrated approach reduces computer resources by removing the need for a user to access multiple different computer systems to gather information about dose calculations. At the same time, this approach optimizes the use of computer resources associated with generating and providing alerts to a user. This approach provides advantages over prior systems. For example, some prior systems require a user to create and send emails to caregiver users every time an alert condition is detected, requiring the cooperation of multiple computer systems to generate, send, and relay the email to the caregiver's inbox. The disclosed embodiments may provide informative alerts selectively and within the same user interface, to inform the caregiver to an alert condition at the point of care and at the time care will be provided, thereby reducing the computer resources needed to generate and send emails while enhancing the caregiver's experience.

FIG. 1 illustrates an exemplary system environment 100 for implementing embodiments consistent with the present disclosure, described in detail below. As shown in FIG. 1, system environment 100 includes several components. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 includes a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processor 140 and one or more databases 150 (e.g., an electronic health record (EHR) database), which are illustrated in a region bounded by a dashed line representing system 130 in FIG. 1. Processor 140 may comprise at least one processing device, such as one or more generic processors, e.g., a central processing unit (CPU), a graphics processing unit (GPU), or the like and/or one or more specialized processors, e.g., a application-specific integrated circuit (ASIC), a field-programmable gate array (FPGA), or the like.

In one embodiment, system 130 may transmit and/or receive data to/from various other components, such as one or more data sources 110 and client device 160. More specifically, system 130 may be configured to receive and store the data transmitted over a network 120 (e.g., the Internet, an Intranet, WAN, LAN, cellular network, Bluetooth, etc.) from various data sources, including data sources 110, process the received data, and transmit data and results based on the processing to client device 160.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

Data sources 110 may include a variety of sources of medical, terminology, and administrative data. Data stored in data sources 110 may be stored as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, stored data may be in a database format or other structured or non-structured format optimized for enabling system 130 to perform the operations discussed herein.

In some embodiments, system 130 may be configured to receive treatment regimen data 170 from EHR database 150, from a remote database via network 120, or from another storage device in communication with system 130. In some embodiments, treatment regimen data 170 may include information received via input from a user operating client device 160. Treatment regimen data 170 may include, for example, data indicating a prescribed course of treatment for the patient corresponding to a diagnosed medical condition, illness, or disease for the patient. For example, treatment regimen data 170 for a cancer patient may include information about one or more chemotherapy cycles and the associated medications and medication doses and dosages prescribed for chemotherapy. In some embodiments, treatment regimen data 170 may include information about one or more radiation sessions or other treatments identified for the patient condition and treatment regimen. In some embodiments, treatment regimen data 170 may include treatment parameters or guidelines established by a medical research center such as the National Institute of Health, National Cancer Institute, or National Comprehensive Cancer Network. In some embodiments, system 130 may access treatment guidelines from one or more remote systems or one or more communication networks such as network 120.

System 130 may be configured to receive medication data 180 from data sources 110 and/or EHR database 150. Medication data 180 may be stored in a format similar to those previously discussed with respect to treatment regimen data 170, and medication data 180 may be received in a manner such as those discussed with respect to treatment regimen data 170. Medication data 180 may include information about medications or other forms of treatment therapy set forth in a patient's treatment regimen. For example, medication data 180 may include maximum drug doses or guidelines for particular medications or data correlating medication doses to attributes of a patient such as height, weight, body surface area, gender, age, and any other attributes pertinent to medication doses or administration rules. Medication data 180 may be received from one or more third party systems such as those discussed with respect to treatment regimen data 170. In some embodiments, medication data 180 may be received from one or more third party systems operated by drug manufacturers, treatment device manufacturers, or research laboratories.

System 130 may be configured to receive patient attribute data 190 from EHR database 150 and/or data sources 110. Patient attribute data 190 may be stored in a format similar to those previously discussed, and may be received in a manner such as those discussed with respect to treatment regimen data 170. In some embodiments, patient attribute data 190 may include current and historical measurements, vital signs, lab reports, and other current, historical, or predicted information pertinent to a patient's well-being or physiological condition. In some embodiment, patient attribute data 190 may include physiological data entered into one or more client devices 160, sensed by one or more sensor devices associated with the patient, or entered into another computing device associated with the patient such as the patient entering information into a smartphone application.

System 130 may be, for example, an EHR system and may include an EHR database 150. EHR database 150 may store patient EHR records, where each patient may be associated with one or more records generated by one or more health care professionals or by the patient. For example, a caregiver such as a doctor associated with the patient, a nurse associated with the patient, a physical therapist associated with the patient, or the like, may generate an EHR for the patient. In some embodiments, one or more records may be collected and/or stored in the same database. In other embodiments, one or more records may be distributed across a plurality of databases. In some embodiments, the records may be stored and/or provided as a plurality of electronic data representations. For example, the EHRs may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, a patient EHR may include, for example, identification information (e.g., name, address, gender, date of birth, etc.), medical history information (e.g., treatment dates, surgical history, prescribed medicines, family medical history, etc.), provider information (e.g., primary insurance provider, copay amount, secondary insurance provider), and/or contact information (e.g., emergency contact information, primary care provider contact information, etc.).

System 130 may further communicate with one or more client devices 160 over network 120. For example, system 130 may be configured to receive, from client device 160 or another data input or measurement device, input indicative of a treatment regimen, patient attributes, lab test results, treatment regimen progress data, and/or medication data to add to a patient EHR. Client device 160 may include any device capable of receiving or transmitting data over network 120. For example, client device 160 may include a computing device, such as a server, or a desktop or laptop computer. Client device 160 may also include other devices, such as a mobile device, a tablet, a wearable device (e.g., smart watches or other computing devices capable of being worn on a user's body), a virtual machine, or other various technologies. In some embodiments, client device 160 may transmit queries for patient treatment and medical information over network 120 to system 130, such as a query for a treatment regimen and information about medication or therapy in the regimen. In embodiments in which EHR database 150 is a remote database, system 130 may transmit queries via network 120 to retrieve, create, edit, or delete EHR information associated with a patient.

Figure 2:
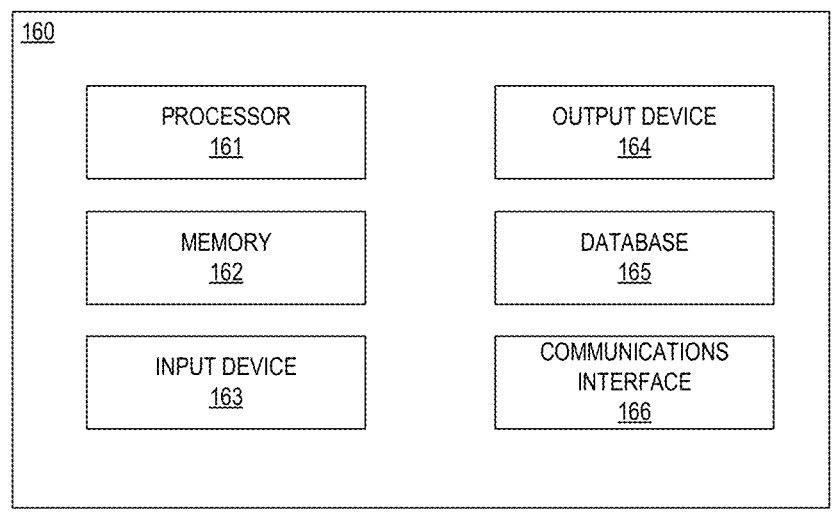
FIG. 2 is a block diagram illustrating an exemplary computing device for performing operations consistent with the present disclosure.

FIG. 2 is a block diagram illustrating an exemplary client device 160. Computing device 102 may include at least one processor (e.g., processor 161), a memory 162, an input device 163, an output device 164, a database 165, and a communication interface 166.

Processor 161 may be configured to perform one or more functions described in this application. Client device 160 may also include a memory 162 that may store instructions for various components of client device 160. For example, memory 162 may store instructions that, when executed by processor 161, may be configured to cause processor 161 to perform one or more functions described herein.

Input device 163 may be configured to receive input from the user of client device 160, and one or more components of client device 160 may perform one or more functions in response to the received input. In some embodiments, input device 163 may include a keyboard or keypad integrated within client device 160, or in communication with processor 161. In some embodiments, input device 163 may include an interface displayed on a touchscreen (e.g., output device 164). Output device 164 may be configured to output information and/or data to the user such as a caregiver. For example, output device 164 may include a display configured to display patient information. In some embodiments, output device 164 may include a touchscreen. In some embodiments, input device 163 may include a camera, microphone, or physiological sensor for collecting data associated with a patient.

Database 165 may be configured to store various data and information for one or more components of client device 160. For example, database 160 may store some or more of treatment regimen data 170, medication data 180, or patient attribute data 190. In some embodiments, database 165 may be partially or fully synchronized with data sources 110 and/or EHR database 150.

Communication interface 166 may include one or more devices or circuits for connecting client device 160 to network 120. In some embodiments, communication device may include a network adapter, antenna, communication port, or other device that enables client device 160 to communicate via wired or wireless techniques with network 120. In some embodiments, communication interface 166 may include additional components for enabling additional communication links with other devices and networks (not shown), such as Bluetooth links between client device 160 and other devices shown in environment 100 or devices not shown, a cellular link between client device 160 and a cell tower, a satellite link, and other communication techniques suitable for use with the disclosed operations.

Figure 3D:
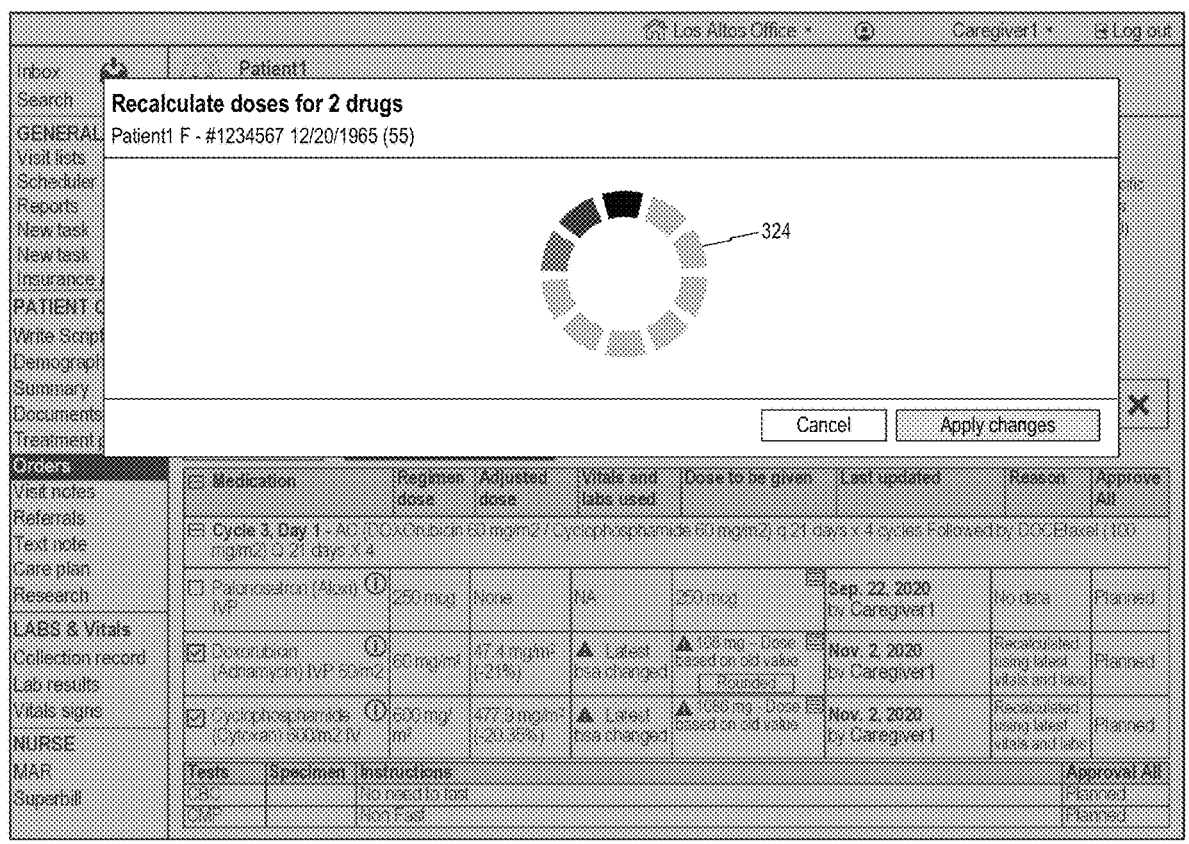

FIGS. 3A-3E are illustrations of exemplary GUIs for recalculation alerts and dynamic multi-layered graphical user interfaces to allow a user to recalculate doses, consistent with the present disclosure. As shown in FIG. 3A, orders page 300 may include an identification of a patient and patient information along the top portion 302 of the GUI, with information such as a name, sex, date of birth (DOB), and facility room number (if any) for the patient. Orders page 300 may also identify an attending caregiver such as a physician associated with the patient. Orders page 300 may also include a main portion 304 for providing details about medications ordered for the patient's treatment regimen. As shown in portion 304 of the example in FIG. 3A, patient attributes are displayed for the patient's body surface area (BSA), weight (Wt), height (Ht), known allergies, and diagnoses, and relevant lab results such as serum creatinine levels. Treatment regimen data may also be displayed to indicate treatment regimens associated with the patient diagnoses. Orders page 300 may provide a table 306 or other structured display of medication information associated with the treatment regimen. In some embodiments, table 306 may allow a caregiver user to scroll through a list of medications. Table 306 may provide information from one or more of treatment regimen data 170, medication data 180, and/or patient attribute data 190. As shown, table 306 may provide medication name and details from medication data 180. A regimen dose may be determined by system 130 based on medication doses specified in treatment regimen data 170 and/or medication data 180. As shown, the value in the regimen dose or adjusted dose columns may be specified per $mg/m^2$ of a patient's body size, and the actual dose to be administered (as shown in the "Dose to be given" column), may be calculated by taking into account "Regimen dose" or "Adjusted dose" and a patient's body size. The "Regimen dose" refers to the dose provided in a treatment guideline or other source, and the "Adjusted dose" refers to a deviation from the "Regimen dose." When determining whether to make an adjustment to the Regimen dose, things like a patient's vitals and labs, or other attributes, may be considered. Other reasons a user may apply an adjustment to the regimen dose may include, a patient's allergies, reaction to a drug treatment (e.g., a patient is experiencing excessive toxicity, and therefore need a reduced dose), and/or a patient current state (e.g., the dose may need to be reduced for a patient in a weakened state). If the regimen dose has not been adjusted from the Regimen dose, orders page 300 may indicate "None" or "N/A" in an adjusted dose column.

If a regimen dose has been adjusted, the adjusted dose column may indicate updated information including, for example, the new dose, and a graphical indicator of the difference between the recommended dose regimen and adjusted doses. In the example shown, a percentage change may be calculated and displayed. The GUI may provide contextual information for a caregiver user including, for example, an indication of the "vitals and labs used" in calculating the appropriate dose to administer to a patient. The "vitals and labs used" may also indicate a warning that vitals and labs have changed since a treatment dose was last calculated, and therefore, the dose should be recalculated. In the example shown in FIG. 3A, the GUI indicates that the patient's body surface area (BSA) changed, causing system 130 to trigger an alert 308 to recalculate the medication doses, and/or activate a selectable recalculation button 309 to perform a recalculation. If a dose is recalculated or adjusted, the dose to be given may be updated and a date and caregiver name associated with the updated dose, a reason for updating the dose, and an approval status for the medication doses may be displayed in the respective columns indicated in GUI 300. If a patient's vitals and labs have changed since a treatment dose was calculated, and recalculation has not been performed, then system 130 may display a warning in the "Doses to be given" column that the values displayed are based on old values. In some embodiments, one or more alert icons may appear within portions of table 306, such as alert icons displayed in the "Vitals and labs used" and "Dose to be given" columns of table 306. For example, a warning may be displayed in the "Vitals and labs used" column that there has been a change. Until the dose is recalculated, the warning may continue to display in the "vitals and labs used" and "Doses to be given columns." Once recalculation has been performed, then these warnings may disappear until the next triggering event.

In some embodiments, system 130 may automate the process of analyzing a combination of treatment regimen data 170, medication data 180, and/or patient attribute data 190, in order to dynamically adjust the appearance of one or more graphical user interfaces and generate additional user interface layers. In some embodiments, system 130 may identify patient attribute data 190 associated with the treatment regimen or medications in the treatment regimen, and extract the associated patient attribute data. In the example shown in FIG. 3A, system 130 has analyzed regimen doses for medications in treatment regimen data 170, a body surface area measurement recently taken and stored in patient attribute data 190, and optionally thresholds identified in medication data 180, and evaluate one or more predefined rules for regimen doses. In some embodiments, system 130 may evaluate one or more conditions of the predefined rules to determine whether or not the condition(s) have been met or satisfied, and the result of this evaluation may prompt system 130 to generate and provide a recommendation or request for dose recalculation. In some embodiments, a rule may be satisfied when a predefined rule condition is met, or a predefined threshold is met and/or exceeded. In some embodiments, system 130 may determine that a rule condition is not satisfied when a predefined threshold is not met, or values are within a predefined range for the rule. The disclosed embodiments are not limited to a particular determination that rule conditions are satisfied/met or not satisfied/met.

In some embodiments, a result of the predefined rule condition evaluation may trigger an alert and cause system 130 to take one or more actions such as displaying an alert to a user or activating a selectable button. In some embodiments, system 130 may periodically determine whether one or more predefined rules are met, such as on a predefined schedule. In some embodiments, system 130 may apply the predefined rules and perform this determination upon loading the interface for a particular patient. System 130 may compare extracted patient attributes (such as body weight or body surface area) to one or more thresholds in one or more predetermined rule sets. In some embodiments, the rule sets may correlate a dose amounts of medications to expected values of patient attribute data. For example, a predetermined rule set may correlate different body weight or body surface areas with different dose amounts of a particular medication. As shown in FIG. 3A, if the predefined rule is met then an alert may be triggered, and the GUI may display one or more interactive icons to alert a caregiver user, and system 130 may generate for display an information box explaining that vitals and labs used to calculate medications have changed by a threshold amount since the dose were last calculated. In some embodiments, system 130 may store a set of predefined rules for setting thresholds and tolerances that associate potential changes in patient attribute data 190 with a need to recalculate medication doses. For example, in some embodiments, a predefined rule may associate a threshold percentage change in body weight or body surface area with an alert trigger. As another example, a predefined rule may associate any detected change in a serum creatinine level with an alert trigger. As yet another example, a predefined rule may associate entry of any new lab type with an alert trigger for recalculating dose amounts. Responsive to a determination that one or more of the predefined rules have been satisfied or that an alert is triggered, system 130 may generate and display a selectable button for recalculating medication doses associated with the satisfied rule. In some embodiments, the recalculation button 309 may be displayed in the interface, but may only be selected and activated by a user once system 130 identifies a need to recalculate medication doses (e.g., the recalculation button 309 may be non-selectable until it is activated). In some embodiments, the recalculation button 309 may be displayed dynamically and appear in the display once activated. In some embodiments, the GUI may also include one or more buttons that, if selected, would allow a caregiver user to manually adjust regimen doses independent of any recommendation by system 130 to change a dose. In some embodiments, system 130 may activate and/or restrict activation of recalculation button 309 based on a user's role. For example, if system 130 determines that the user is a caregiver, system 130 may associate a user permission with the caregiver account that causes system 130 to activate the recalculation button 309. Some users account types, such as admins or other accounts that are not associated with treating the patient, may have restricted permission settings so that system 130 will not activate the recalculation button 309.

After detecting selection of an active "recalculate" button, system 130 may generate for display a graphical user interface such as the example shown in FIG. 3B. FIG. 3B shows a recalculate doses interface 310, which may appear as floating box layered over the orders GUI 300 of FIG. 3A. System 130 may automatically identify one or more medications in the patient's treatment regimen requiring recalculation due to a condition being met or satisfied in one or more predefined rules. The identified medications may be displayed in a medications table 312 in interface 310, in conjunction with the regimen dose, any adjustment to the regimen dose, changes in vitals and/or labs that system 130 has detected since the calculation of last dose amounts, and changes to the "Doses to be given," as calculated by system 130. System 130 may also generate for display a notation 314 for visually indicating how the dose changed and the underlying variables contributing to the change. In the example shown, the patient's change in body surface area (BSA) is visually indicated with notation 314 in the form of strikethrough text and an arrow, to quickly inform the caregiver that the patient's BSA changed from 1.81 m$^2$ to 1.65 m$^2$. In the next column, similar visual notations may be used to inform the caregiver how the dose to be administered has changed. In the illustrated example, the first medication dose changed from 108 mg to 100 mg using the recalculation based on the change in BSA.

Interface 310 may include interactive elements allowing input from a caregiver user, to modify the application of dose calculations provided by system 130. For example, the caregiver user may provide a selection of a "reason" 316 to append to the updated dose information in the electronic health record. In some embodiments, system 130 may pre-select one or more displayed "apply changes to" option 318 icons to apply a setting selected by system 130 if the caregiver user does not change the selection(s). System 130 may also provide the user with selectable options for applying the updated dose to a single treatment session or for all future sessions associated with the treatment regimen. Additionally, interface 310 may provide the caregiver user with an interactive button 320 to apply changes to the doses and return to the orders page shown in FIG. 3A. In some embodiments, selection of certain icons may cause system 130 to generate and provide one or more warning messages, such as the warning 322 shown in FIG. 3C after the user has selected to apply changes to all treatment sessions associated with administration of the identified medications. Displayed warnings may be selected in accordance with one or more rule sets associated with the treatment regimen, administrative rules for the medical facility, or administrative rules associated with insurance providers.

Figure 3E:

Following selection of the user interface button to apply changes, system 130 may replace portions of the displayed interface with an animated icon 324 such as the example illustrated in FIGS. 3D and 3E while system 130 updates EHR database 150, data sources, and other memory storage locations with the updated dose information, and reconstructs the interface illustrated in FIG. 3A with the updated dose and reason information. The reconstructed interface in this example may appear similar to the interface 400 depicted in FIG. 4A. FIG. 4A depicts the new dose 402 to be given (e.g., 100 mg of Doxuorubicin instead of 108 mg of Doxuorubicin, as shown in FIG. 3A), updated vitals and labs used, and the reason column has been populated based on selections made in the overlaid interface shown in FIGS. 3B and 3C.

In some embodiments, system 130 may automatically recalculate dose amounts, without prompting a user to select a recalculation button or provide other inputs. Some embodiments may allow for limited automatic recalculations, such as by restricting automatic recalculations to certain medications identified in one or more rule sets. As an example, some embodiments may include automated dose amount recalculations only for the medication Carboplatin. Carboplatin may initially be ordered in a dose unit called an area under the curve (AUC), and this type of unit may need to be closely monitored in relation to a patient's vitals and labs such as lab serum creatinine. If system 130 detects a fluctuation or change in lab serum creatinine that meets or exceeds a predefined change threshold, system 130 may require a dose adjustment to the Carboplatin AUCs. In some embodiments, system 130 may require a higher frequency of vitals and lab measurements for certain medications based on one or more predefined rule sets to ensure safety of the patient. In the current example, a treatment regimen including Carboplatin may be associated with an increased frequency of lab serum creatinine measurements. A measurement frequency may be configured in one or more predefined rules set by the clinic or medical facility. As an example, a predefined rule may require updated serum creatinine labs every 7, 15, or 30 days. At the time Carboplatin is ordered, system 130 may check to determine whether the patient's height and weight is within a predefined range, and determine whether the patient's serum creatinine lab was completed within a predefined time period preceding the order. If these conditions are satisfied, system 130 may automatically calculate the dose amount (e.g., milligrams) of the medication from the AUC. If system 130 determines that the patient's information and labs do not comply with the predefined rules (e.g., the serum creatinine is from 35 days ago), then system 130 may not automatically calculate dose amounts from the AUC, and may not automatically recalculate a prior mg amount.

Figure 4D:
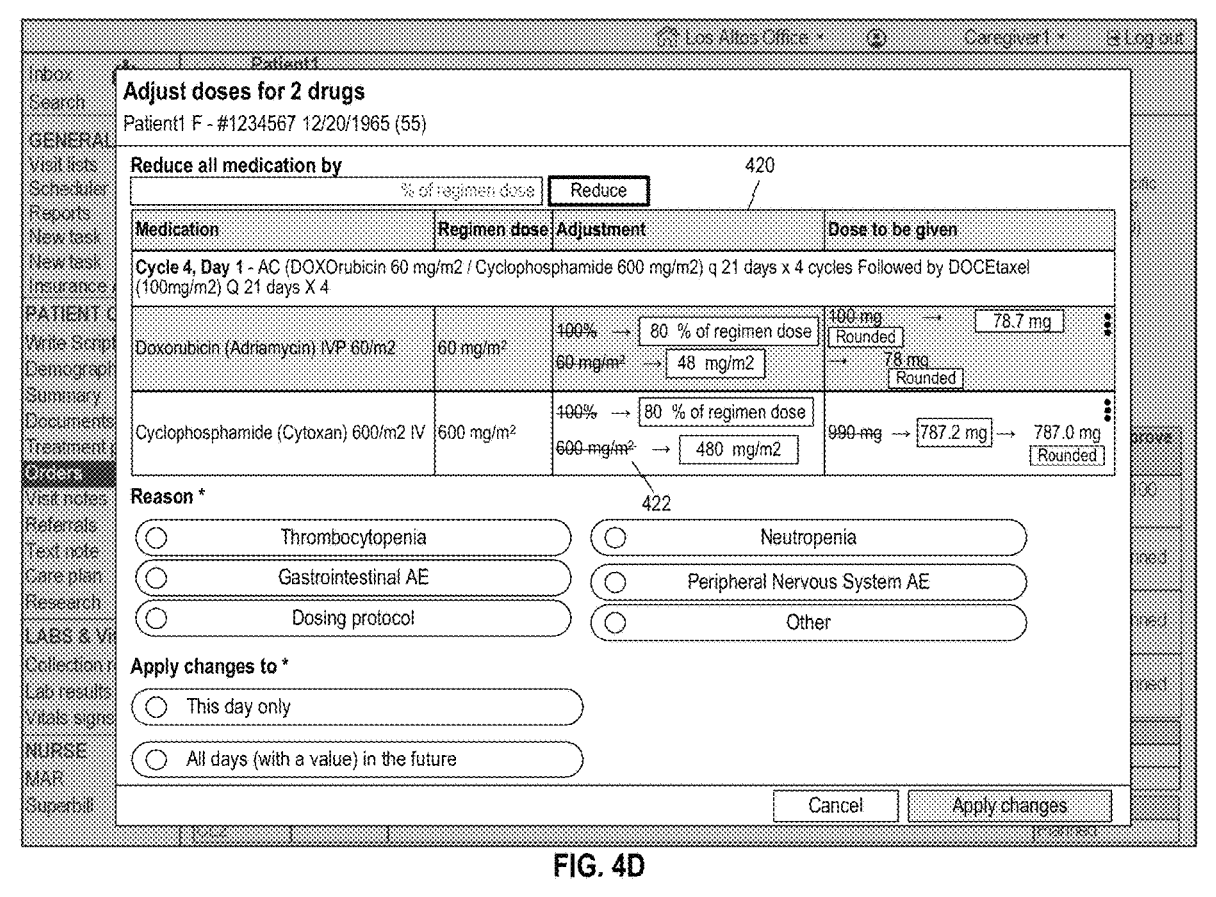
Figure 4F:
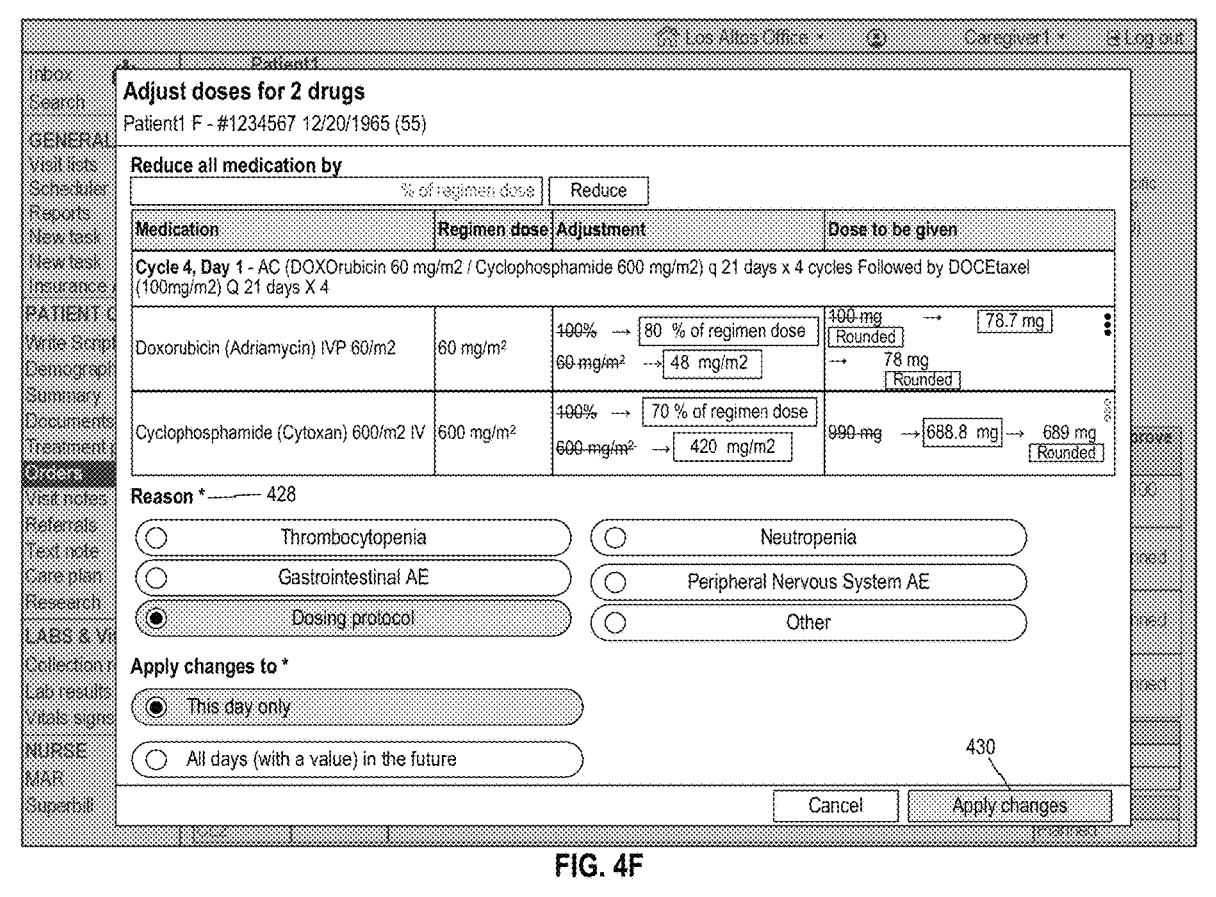
Figure 4G:
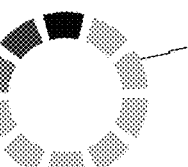

FIGS. 4A-4H are illustrations of exemplary GUIs for dose adjustments, consistent with the present disclosure. In some embodiments, dose adjustments may include changes specified by a caregiver user, in contrast to the recalculations that are performed after an automatic alert generated by system 130, as described in connection with FIGS. 3A to 3E. FIG. 4A shows an updated version of the orders interface depicted in FIG. 3A, following the dose recalculation operations discussed above. As shown in FIG. 4A, system 130 may provide a selectable icon 404 next to each listed medication, such as a check box or toggle switch. In some embodiments, system 130 may also provide a select all icon 406 at the top of the medication list to allow a caregiver user to select all medications with the single select all icon 406. Responsive to a determination that at least one medication icon has been selected, system 130 may activate one or more interactive elements in the user interface, such as buttons for adjusting or recalculating doses. As shown in FIG. 4A, the "Recalculate doses" 408 and "Adjust doses" 410 buttons are displayed in a light color and may not be selected by a user. In some embodiments, system 130 may permit or restrict activation of a dose adjustment button based on user account permissions, such as the permissions previously discussed with respect to recalculation button 309. Following selection of medications, system 130 may activate one or more of the buttons and dynamically change an appearance of the buttons to reflect their updated statuses. As shown in FIG. 4B, system 139 may modify the "Adjust 2 doses" 412 and "Recalculate 2 doses" 414 buttons to correspond to the number of medications selected (2), and the buttons may be displayed in a modified appearance indicating that they are now selectable by a user. In the example shown, the Adjust and Recalculate buttons are displayed with a darker/bolder appearance.

Responsive to a determination by system 130 that the caregiver user has selected at least one medication (two are selected in the illustrated example) and the "Adjust 2 doses" button 412, system 130 may generate for display an overlay interface such as the interface shown in FIG. 4C. As shown, system 130 may automatically populate portions of the overlaid interface with information about the selected medications extracted from medication data 180 and dose information extracted from treatment regimen data 170. In some embodiments, system 130 may identify a set of side effects or potential reasons 416 for adjusting medication doses, based on information extracted from the caregiver user's interaction with the interface. For example, system 130 may identify the selected medications and extract information about the caregiver user's adjustment(s) to the medication. System 130 may then query treatment regimen data 170 and/or medication information 180 to identify potential reasons for adjusting doses, and display the selected reasons in the interface with interactive icons such as radio buttons. Such an interface may allow the caregiver user to quickly append a reason to the dose adjustment, for clarity in the patient's health record.

As shown in FIG. 4C, a caregiver user may input a single reduction percentage 418 to apply to all selected medications. In some embodiments, system 130 may provide user interface controls for individually adjusting medications. FIG. 4C shows a default display with both medications at 100% of their original dose (0% reduction). In this example, if a caregiver user entered "20" into a reduction input field and selected the "reduce" button, system 130 may automatically recalculate doses after a 20% reduction, and display the updated doses and related information in table 420 shown in FIG. 4D. Similar to the discussion with respect to FIG. 3C, system 130 may generate and display visual notations 422 illustrating the adjustment from old to new dose amounts.

FIG. 4E illustrates an individual adjustment applied to a single medication. As shown, both the first and second selected medications may already be reduced by 20% (based on the example shown in FIG. 4D). FIG. 4E further shows that a caregiver user may select a particular medication to apply an individualized dose reduction. In the example shown in FIG. 4E, the dose for the second medication 424 identified for adjustment was reduced by 30% in response to input from the caregiver user. System 130 may generate and display visual notations 426 illustrating the adjustment from old to new dose amounts, consistent with previous discussions.

Referring to FIG. 4F, system 130 may detect user input indicative of a selection of a reason 428 for the dose adjustment, and a setting for applying the dose adjustment to a single treatment session or all future treatment sessions involving the identified medications, consistent with prior discussions. After detecting selection of a button 430 for applying changes, system 130 may replace portions of the user interface with an animated icon 432 such as the example illustrated in FIG. 4G while system 130 updates EHR database 150, data sources, and other memory storage locations with the adjusted dose information, and reconstructs the interface illustrated in FIG. 4A with the updated dose and reason information. The reconstructed interface in this example may appear similar to the interface 440 depicted in FIG. 4H, showing the adjusted dose, new dose to be given, and the reason column populated based on selections made in the overlaid interface shown in FIGS. 4D, 4E, and 4F.

Figure 5:
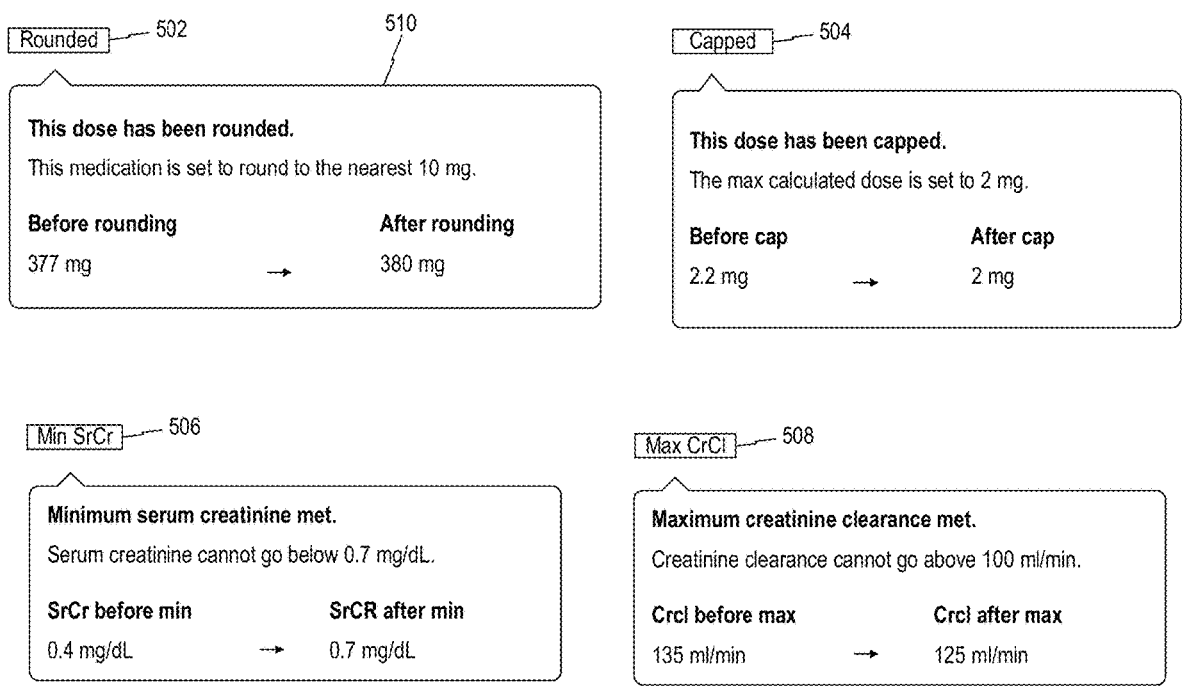
FIG. 5 is an illustration of exemplary GUI elements for medication table badges, consistent with the present disclosure.

FIG. 5 is an illustration of exemplary GUI elements for medication table badges, consistent with the present disclosure. In some embodiments, system 130 may generate and display one or more interactive graphical elements that may trigger the display of an overlay window shown as a layer over the user interface. The graphical elements may appear as icon-like badges having a descriptive appearance that provides high-level information to a caregiver user about information displayed in the GUI. FIG. 5 shows examples of the badges as the "Rounded" badge 502, "Capped" badge 504, "Min SrCr" badge 506, and "Max CrCl" badge 508. The examples shown are meant to be non-limiting, such that some embodiments may include additional types of badges that may provide high-level contextual information coupled with a detailed overlay interface based on uses interaction with the badge.

System 130 may automatically generate and display one or more of these badges to provide a caregiver user with contextual information about the displayed values. The badges may be displayed adjacent to a relevant value in the user interfaces disclosed herein. For example, in the interface shown in FIG. 4D, a dose to be given of Cyclophosphamide (Cytoxan) was calculated to be 787.2 mg, by determining 80% of the original 990 mg dose. System 130 may apply one or more rule sets to calculated values, such as rounding values up or down depending on a threshold associated with a round-up or round-down rule. In the example shown, the 787.2 mg dose is rounded down to 787.0 mg. System 130 may provide a "Rounded" badge 502 directly beneath or next to the rounded dose to inform a caregiver user that the displayed dose has been rounded from the originally-calculated dose.

In the examples shown, "Capped" badge 504 may be associated with a rule that is set in the formulary entry of a particular drug. For example, a patient should never receive more than 10 mg of drug X. Drug X may be capped at 10 mg, and "Capped" badge 504 may indicate that the associated drug may not exceed a predefined dose. The "Min SrCr" badge 506 may correspond to a serum creatinine (or SrCr) lab value used to calculate a dose of a particular drug. If a patient's SrCr value is below a minimum predefined value set by the facility in one or more predefined rules, then system 130 may rounds the value up to the minimum. The "Max CrCl" badge 508 may correspond to a creatinine clearance (or CrCl), a value used to calculate a dose of a certain drug. In some embodiments, if system 130 determines that the CrCl value for a patient exceeds a maximum value set by the facility in one or more predefined rules, then system 130 may use a maximum value to calculate the dose.

Displayed badges may designate an interactive portion of the graphical user interface, such that system 130 may monitor for user interactions with the displayed badges. For example, system 130 may track a location of a mouse cursor, a pointing device on a touch screen, or a location of any other suitable type of pointing device, and detect when the location corresponds to a displayed badge. Upon such a detection, system 130 may dynamically modify the displayed interface to provide an additional layer of information associated with the displayed badge. In some embodiments, system 130 may require detection of a mouse click or other action to select the badge, to prevent the unnecessary generation and display of additional interface layers. In some embodiments, system 130 may provide additional interface layers without requiring a click or other selection action, to provide information to caregivers as quickly as possible, and to enhance the user's experience by dynamically changing the interface appearance without the need for repeated selections by a user.

FIG. 5 also shows examples of graphical interface layers associated with displayed badges. As one example, selection of the "Rounded" badge may cause system 130 to provide and overlay an interface layer 510 explaining that the dose value has been rounded, providing the rounding rule employed by system 130, and providing both the unrounded and rounded values. By dynamically adjusting the graphical user interface to provide multiple layers of information based on user interaction with the badges, several of the technical advantages of the disclosed embodiments can be realized, including the conservation of computer resources until additional information layers are required. Furthermore, the user experience is enhanced through the generation of a concise user interface coupled with information layers that provide the additional information necessary for a caregiver user to understand the dose calculations without the need to access other computer systems or other software applications.

Figure 6:
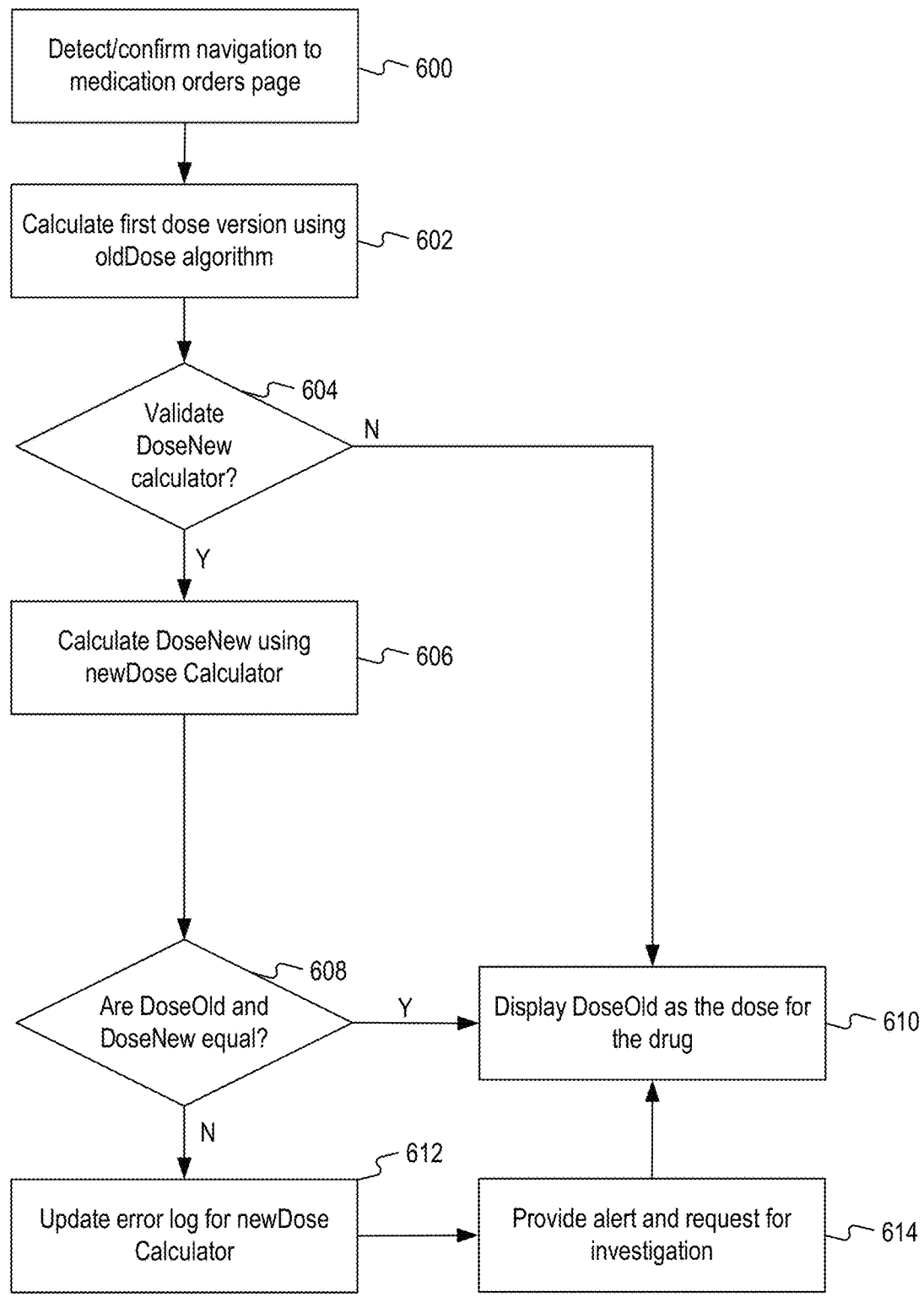
FIG. 6 is a flowchart for an exemplary dose calculator validation process, consistent with the present disclosure.

FIG. 6 is a flowchart for an exemplary dose calculator validation process, consistent with the present disclosure. In some embodiments, system 130 may execute one or more background operations to verify recalculated dose amounts. Such embodiments may employ different dose calculation algorithms to confirm that the algorithms are properly programmed to provide accurate dose calculations. As shown in FIG. 6, the process may begin at step 600 with system 130 detecting or confirming that a caregiver user has navigated to a medication orders page of the user interfaces. In some embodiments, system 130 may also determine whether any doses have been identified as requiring recalculation or adjustment (not shown). In some embodiments, however, system 130 may perform the validation process for all medication doses regardless of a perceived need to recalculate. At step 602, system 130 may calculate a first version of a medication dose using a first dose calculator algorithm previously stored and recalled by system 130 or accessed from a third party system by system 130. As shown in the example flowchart, the first algorithm may be an "old" algorithm having a prior set of rules or calculations as compared to the second algorithm used in this process. In some embodiments, the first dose calculation algorithm may be one that that has been previously verified, and can serve as a benchmark for testing a second dose calculation algorithm. At step 604, system 130 may determine whether a second dose calculator algorithm (such as a "new" calculator) should be validated. Responsive to a determination that a second, new dose calculator should be verified ("Yes" in step 604), in step 606, system 130 may proceed to calculate a second version of the same medication dose using a second dose calculator algorithm previously stored and recalled by system 130 or accessed from a third party system by system 130. In step 608, system 130 may compare the first and second dose calculations and determine whether they are the same. In some embodiments, system 130 may set or store an equality threshold, such as a predefined tolerance range or percentage, such that if the calculations are within the range or percentage then system 130 may treat the results as the "same." If system 130 determines that the calculations are the same ("Yes" in step 608) then system 130 may provide the first dose calculation to the caregiver user via the user interface (step 610). In some embodiments, the user interface may provide an indication such as a badge informing the caregiver user that the dose calculation is verified. In other embodiments, the user interface may simply provide the calculated dose without a badge.

Responsive to a determination that the first and second dose calculations are not the same ("No" in step 608), system 130 may identify an error and update an error log for the second dose calculation algorithm (step 612). In some embodiments, system 130 may provide one or more alert messages to an engineering team to investigate the discrepancy between the first and second dose calculation algorithms (step 614). System 130 may then provide the first dose calculation calculated by the first dose calculation algorithm (step 602) for output in the user interface at step 610.

Returning again to step 604, responsive to a determination that a new calculator should not be verified ("No" in step 604), system 130 may proceed to step 610 provide the first dose calculation calculated by the first dose calculation algorithm (step 602) for output in the user interface.

Figure 7:
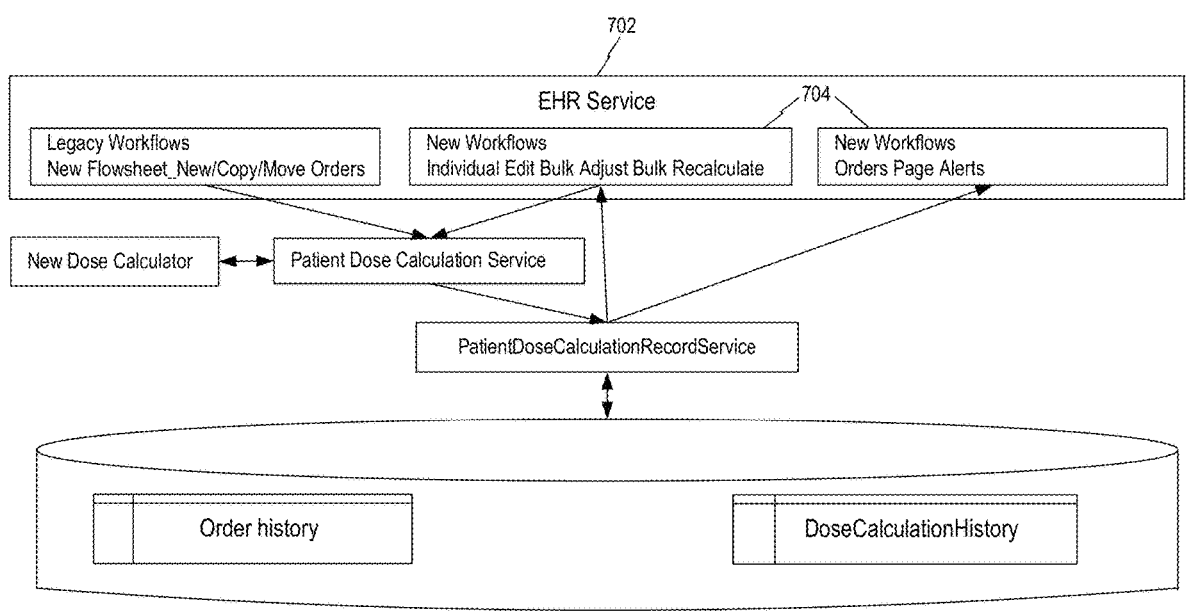
FIG. 7 is a block diagram for a dose calculation service architecture, consistent with the present disclosure.

FIG. 7 is a block diagram for a dose calculation verification service architecture, consistent with the present disclosure. Dose calculation verification may be performed when dose recalculations are performed. As shown, one or more databases, such as EHR database 150 and/or data sources 110, may store medication order history information and a history of dose calculations for a patient. In some embodiments, this information may be stored within the data files for one or more of treatment regimen data 170, medication data 180, or patient attribute data 190. The database(s) may interface with a patient dose calculation record service module, which may include one or more data storage and retrieval algorithms capable of performing the operations disclosed herein. In some embodiments, the record service module may be employed using an individual processor of system 130, an individual processor of client device 160, or a dedicated processor for one or more of data sources 110. In some embodiments, a single processor within environment 100 may be configured to perform the functions of the operations and software modules disclosed herein.

The service architecture shown in FIG. 7 may also include an EHR service 702, including legacy workflows and new workflows for performing operations such as creating new medication orders, copying or moving medication orders, adjusting or recalculating individual or bulk medication doses, recalculating medication doses, and for providing order page alerts. As shown in the figure, legacy workflows for creating new orders, copying orders, or moving orders may interface with a Patient Dose Calculation Service module, which may have the functionalities previously discussed with respect to calculating and verifying patient medication doses determined during dose recalculation. In some embodiments, some new workflows for dose adjustment and recalculation may also interface with the Patient Dose Calculation Service module.

In some embodiments, the Patient Dose Calculation Service module may employ a new calculator, as discussed in connection with FIG. 6, retrieved from one or more research organizations or third party systems. The Patient Dose Calculator Service module may interface with the Record Service module, to provide updated medication dose information for storage in data sources 110, EHR database 150, or other data storage locations previously discussed.

In some embodiments, the Record Service module may interface with the dose adjustment/recalculation workflows and other new workflows for providing alerts via the user interface. The rule satisfaction logic may be performed within front-end code executed by system 130. In some embodiments, rule logic may be encapsulated by "New Workflows" 704 of FIG. 7. For example, the Record Service module may be used to identify a rule satisfaction prompting a recommendation to recalculate medication doses, or prompting system 130 to generate and provide one or more alert icons, as discussed in further detail below. In further embodiments, the Record Service module may provide patient, medication, and treatment data from System 110, providing enough information to system 130 so that system 130 may determine whether or not to recommend a recalculation, and thus generate and provide one or more alert icons.

Figure 8:
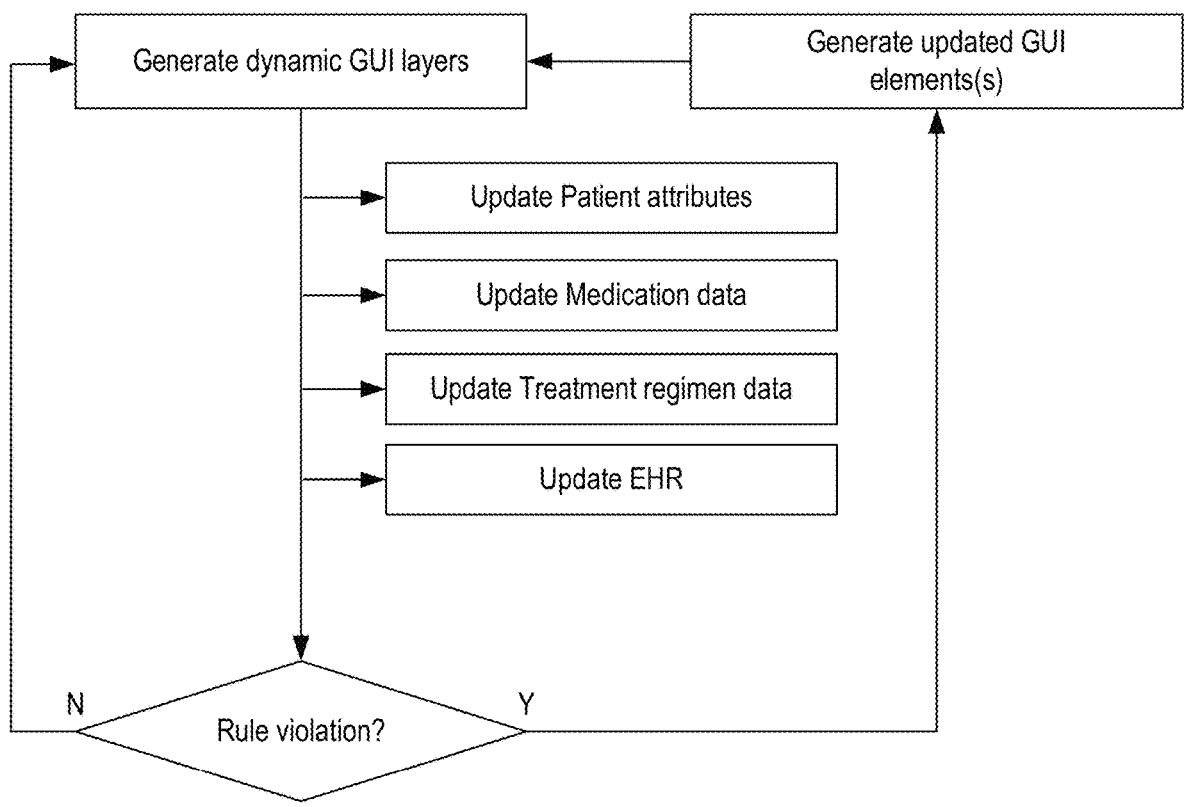
FIG. 8 is a block diagram and flowchart for an exemplary system architecture for generating and providing GUI alerts, consistent with the present disclosure.

FIG. 8 is a block diagram and flowchart for an exemplary system architecture for generating and providing GUI alerts, consistent with the present disclosure. In some embodiments, system 130 may generate and provide one or more alert icons associated with a perceived rule satisfaction or need to adjust/recalculate medication doses. As shown, system 130 may operate in a continuous loop of generating a dynamic GUI with multiple layers. During the generation and display of the GUI layers, system 130 may continue to monitor for updates in patient attribute data 190, treatment regimen data 170, and medication data 180. System 130 may also continue to compare combinations of data to one or more rule sets to detect a rule satisfaction. If no rules are satisfied (indicating that recalculation is not necessary), system 130 may continue to generate and display the dynamic GUI layers without alerts or notifications. If a rule satisfaction is detected, system 130 may generate updated GUI elements corresponding to alert conditions or notifications that are identified for displaying to a caregiver user.

In some embodiments, system 130 may be configured to generate one or more GUIs with a report of patients associated with dose recalculations within a defined time period. In some embodiments, system 130 may generate reports identifying information associated with the dose recalculations, such as identification of rule conditions that were met and triggered one or more alerts and recalculation prompts.

The disclosed embodiments provide improvements over traditional alerting systems. Traditional systems often overload caregivers with alert messages when there is no pressing need for the caregiver to take action. For example, traditional systems may provide too many alerts to caregivers on a daily basis, causing alert fatigue as caregivers must frequently review the alerts to make decisions as to whether the alerts are actual cause for concern or action. The disclosed embodiments provide functionality for generating and providing new types of alerts, and these alerts are purposefully accompanied by visual explanations for the alert in multiple layers. The disclosed embodiments provide graphical user interfaces that present alerts at the point of care within the exact workflow where caregivers will review doses for a particular treatment and seek administrative/insurance approval for the treatment, as opposed to many alerts that are sent to a caregiver's email inbox, and can't be actioned on at the point of care. Thus, the alerts of the disclosed embodiments are timely, informative, selective, and within the workflow.

Figure 9:
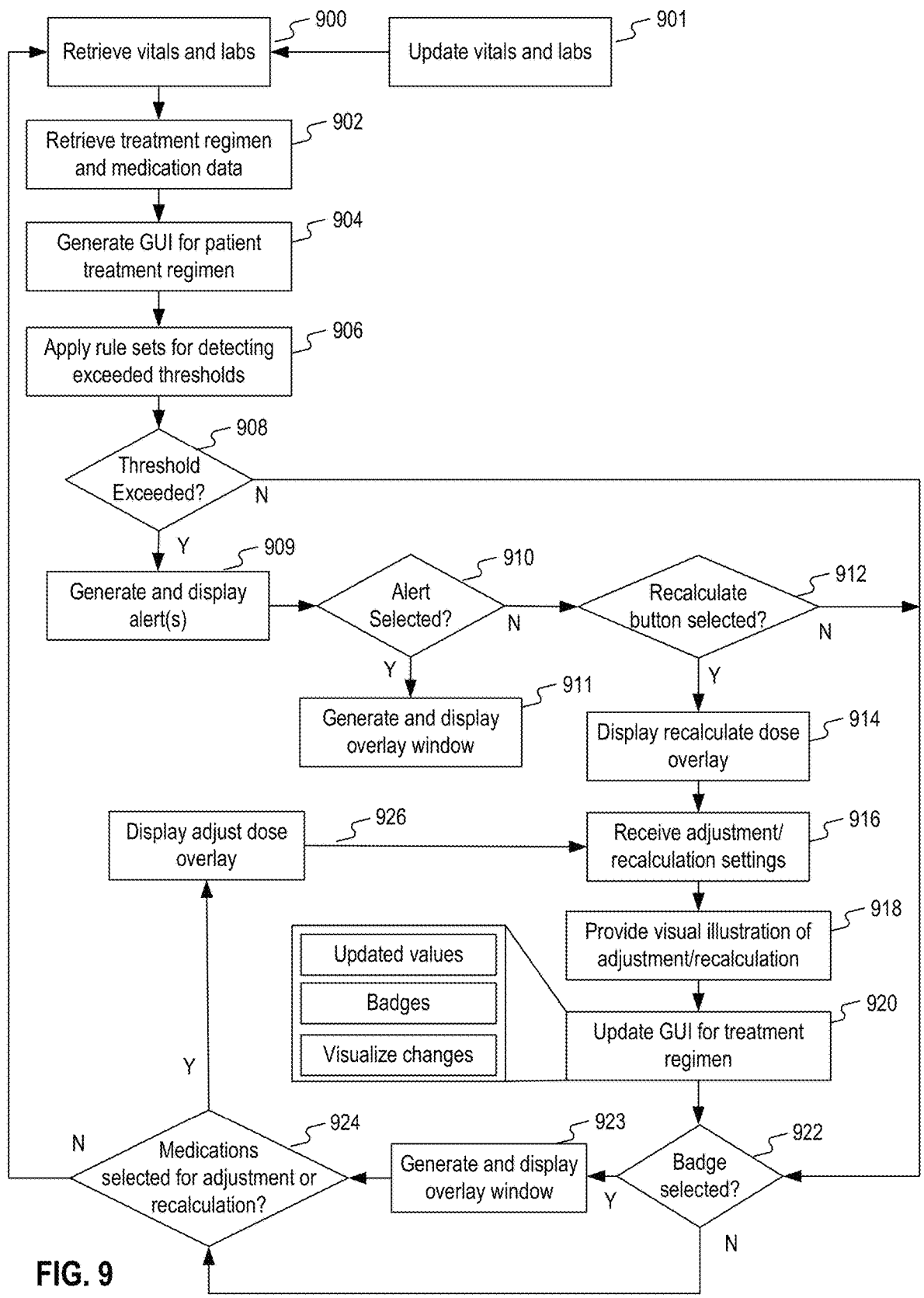
FIG. 9 is a flowchart of an exemplary process for generating dynamic multi-layered graphical user interfaces for dose recalculation and adjustment, consistent with the present disclosure.

FIG. 9 is an exemplary process for dose recalculation, consistent with the present disclosure. In some embodiments, processor 140 of system 130 may perform operations of the illustrated process. In some embodiments, however operations of the illustrated process may be performed by multiple computing devices of environment 100 of FIG. 1 as well as additional computing devices not shown in FIG. 1. Furthermore, the process illustrated in FIG. 9 is not limited to a particular sequence of steps, and those of ordinary skill in the art will appreciate that some operations may occur in different orders, and that the illustrated process may include additional operations not shown, as well as fewer operations not shown.

In step 900, system 130 may retrieve vitals and labs for a patient, such as by retrieving patient attribute data 190 from data sources 110 and other information from an electronic health record such as EHR database 150. In some embodiments, system 130 may receive updated vitals and labs in step 901, such as new lab results and updated measurements for a patient inputted by a sensor device or by a user via client device 160.

In step 902, system 130 may retrieve treatment regimen and medication data from data sources 110 and/or EHR database 150.

In step 904, system 130 may generate a graphical user interface reflecting the retrieved information for a patient's treatment regimen. System 130 may apply one or more rule sets for detecting exceeded thresholds in step 906 and evaluate one or more rule conditions to determine whether a rule is satisfied or met, or not satisfied (depending on the rule set, condition, and associated trigger). For discussion purposes, the illustrated example evaluates a rule condition to determine whether a threshold has been exceeded, but the disclosed embodiments are not so limited. If a threshold has been exceeded ("Yes" in step 908), system 130 may generate and display one or more GUI elements indicating an alert in step 909. If no thresholds have been exceeded ("No" in step 908), the process may proceed to step 922 (discussed further below).

Following the display of alert GUI elements, system 130 may determine whether an alert GUI element has been selected in step 901. If so ("Yes" in step 910) system 130 may generate and display a window in an overlay layer for providing additional information about the alert, in step 911. If no alert GUI element was selected ("No" in step 910) then system 130 may determine whether a recalculation button (such as the "Recalculate Doses") button has been selected in step 912.

In some embodiments, system 130 may provide one or more selectable buttons for silencing or "dismissing" the alert (such as the X shown in alert 308 of FIG. 3A), that when selected, may cause system 130 to hide the GUI alert for the duration that system 130 is displaying the GUI.

In some embodiments, the dismiss functionality and selectable button(s) may persist across multiple screen visits (e.g., continue displaying the dismiss button(s) if system 130 ceases display of an orders page, displays a different page, and then then displays the orders page again). In some embodiments, system 130 may display persistent dismissal buttons across different pages (e.g., displaying a dismissal button on both an Orders page and a Medication Administration Record page). In some embodiments, system 130 may display dismissal buttons in a manner that persists across multiple different users (e.g., if one user selects the dismissal button and system 130 hides an alert, the alert is hidden for all user accounts). In some embodiments, system 130 may audit dismissal actions and attribute a dismissal action (e.g., selection of a dismissal button) to the user account that recorded selection of the dismissal button. System 130 may record information associated with the dismissal, including a time or date stamp for associated with the dismissal, and reasons recorded in association with the alert dismissal. In some embodiments, system 130 may provide dismissal buttons that include options to prevent the same alert from recurring at a future date/time.

Responsive to a determination that the recalculate button has not been selected ("No" in step 912), system 130 may determine whether a badge is selected in step 922 (discussed further below). Responsive to a determination that the recalculate button has been selected ("Yes" in step 912), system 130 may generate a GUI layer for recalculating doses and display the layer as an overlay window in step 914. The overlay window may provide details associated with a recommendation for recalculating doses including, for example, patient attributes that exceeded a rule threshold associated with the medication.

After displaying a generated overlay window, in step 916, system 130 may monitor for and receive adjustment or recalculation settings inputted by a user, in addition to settings automatically configured by system 130. Based on the received adjustment/recalculation settings, system 130 may generate and provide a visual illustration of the dose adjustment or recalculation in step 918. Following selection of a button to apply changes, system 130 may update the main GUI layer for the treatment regimen in step 920. In some embodiments, the updated GUI may provide one or more of updated dose values, one or more badges for providing context about the updates, and visual markup illustrating how the values changed.

In step 922, system 130 may determine whether a displayed badge has been selected. If so ("Yes" in step 922), then system 130 may generate and display an overlay window as a new layer on top of the treatment regimen GUI in step 923, and then proceed to step 924. If not ("No" in step 922), system 130 may proceed to step 924, and determine whether any medications have been selected for adjustment on the base treatment regimen GUI.

If system 130 determines that no medications have been selected for adjustment ("No" in step 924"), then system 130 may loop its operations back to step 900. If system 130 determines that at least one medication has been selected for adjustment ("Yes" in step 924"), then system 130 may generate and display an overlay window layer for adjusting doses, and proceed to step 916 as previously discussed.

Figure 10:
FIG. 10 is an illustration of an exemplary GUI for providing alerts in a treatment plan page, consistent with the present disclosure.

FIGS. 10 and 11 provide examples of how the disclosed techniques and graphical user interface elements may be incorporated into interfaces other than an orders page interface. FIG. 10 is an illustration of an exemplary GUI for providing alerts in a treatment plan page, consistent with the present disclosure. A treatment plan page may comprise one or more graphical user interfaces in which a primary caregiver would see and perform dose recalculations. As shown, the treatment plan interface may provide a table or chart showing treatment sessions for a patient, in conjunction with all medications and doses to be provided for each treatment session. Similar to the alerts previously discussed, system 130 may generate and display one or more alert icons indicating that a particular dose has changed. After displaying a selection of the alert icon or determination that a pointing device is pointing to the alert icon, system 130 may generate and provide an overlay window 1002 as an additional GUI layer, providing detailed information underlying the change in dose. As shown, overlay window 1002 may provide information including the patient's previous and latest attributes underlying the dose recalculation, as well as an indication of the percentage change in patient attributes (such as a decrease in BSA by 6.95% or −0.13 $m^2$).

FIG. 11 is an illustration of an exemplary GUI for providing alerts in a Medication Administration Record (MAR) page, consistent with the present disclosure. In some systems, the MAR is an interface page where drugs are documented by a caregiver as being administered. As shown, the MAR page may provide recalculation alert windows and icons similar to those discussed with respect to the orders interface shown in FIGS. 3A and 4A. In some embodiments, the MAR page may provide one or more graphical elements such as alert window 1102, that may block treatment administration when there are any outstanding alerts, thereby requiring the caregiver to perform recalculation or dismissing the alert (dismissal button(s) not shown) before administering the medication.

Figure 12:
FIG. 12 is an illustration of an exemplary GUI for providing a history of administration on an orders page, consistent with the present disclosure.

FIG. 12 is an illustration of an exemplary GUI for providing a history of administration on an orders page. As shown, system 130 may provide one or more graphical elements for enabling the display of a history of administration on the orders page, without requiring navigation to a separate interface page. As shown, an administration history section 1202 may be displayed for a particular medication, in response to selection of a graphical element such as box 1204, which a user could select to expand or collapse information associated with a medication. In the example shown, selection of box 1204 may cause system 130 to display historical entries 1206 and 1208, showing a regimen dose, adjustments, vitals/labs, and dose to be given for each of entries 1206 and 1208 in a table format.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for generating dynamic multi-layered graphical user interfaces, comprising:
   a memory storing instructions; and
   at least one processor, the at least one processor being configured to execute the stored instructions to perform operations including:
   retrieving, from at least one networked database, treatment regimen data for a patient;
   retrieving, from the at least one networked database, patient attribute data for the patient, wherein the treatment regimen data identifies a dose of a medication determined based on a historical measurement of the patient in the patient attribute data;
   generating a graphical user interface reflecting the dose of the medication identified in the treatment regimen data and one or more associated patient attributes, wherein the associated patent attributes are extracted from the patient attribute data and reflect a current measurement of the patient;
   comparing the extracted patient attributes to one or more thresholds in a rule set, the rule set correlating the dose of the medication to one or more expected values of the extracted patient attributes;
   based on the comparison, evaluating at least one condition of at least one rule in the rule set;
   based on the evaluation, generating an interactive icon for display in the graphical user interface; and
   responsive to a selection of the interactive icon, generating an overlay window displayed adjacent the interactive icon, the overlay window providing details associated with the interactive icon.

2. The system of claim 1, wherein the interactive icon is associated with a recommendation to recalculate a dose of the medication.

3. The system of claim 2, the operations further comprising:
   generating an updated dose amount of the medication based on the extracted patient attributes and a predetermined regimen dose associated with the medication; and
   providing the updated dose amount and a visual illustration of a dose amount change in the overlay window.

4. The system of claim 1, wherein
   the extracted patient attributes include a patient weight or patient body surface area, and
   the one or more thresholds identify an upper limit or lower limit associated with a dose amount of the medication.

5. The system of claim 1, wherein the selection of the interactive icon comprises a mouse click or touchscreen input corresponding to the interactive icon.

6. The system of claim 1, wherein the selection of the interactive icon comprises a determination that a pointer location of a pointing device corresponds to a display location of the interactive icon.

7. The system of claim 1, wherein the operations further comprise:
   applying a rule for rounding a dose amount of the medication;
   displaying a rounded dose amount based on the applied rule; and
   displaying an interactive badge adjacent to the displayed rounded dose amount.

8. A computer-implemented method for generating dynamic multi-layered graphical user interfaces, the method being performed using at least one processor, the method comprising:
   retrieving, by the at least one processor from at least one networked database, treatment regimen data for a patient;
   retrieving, by the at least one processor from the at least one networked database, patient attribute data for the patient, wherein the treatment regimen data identifies a dose of a medication determined based on a historical measurement of the patient in the patient attribute data;
   generating, by the at least one processor, a graphical user interface reflecting the dose of the medication identified in the treatment regimen data and one or more associated patient attributes, wherein the associated patent attributes are extracted from the patient attribute data and reflect a current measurement of the patient;
   comparing, by the at least one processor, the extracted patient attributes to one or more thresholds in a rule set, the rule set correlating the dose of the medication to one or more expected values of the extracted patient attributes;
   evaluating, by the at least one processor based on the comparison, at least one condition of at least one rule in the rule set;
   generating, by the at least one processor based on the evaluation, an interactive icon for display in the graphical user interface; and
   generating, by the at least one processor responsive to a selection of the interactive icon, an overlay window displayed adjacent the interactive icon, the overlay window providing details associated with the interactive icon.

9. The method of claim 8, wherein the interactive icon is associated with a recommendation to recalculate a dose of the medication.

10. The method of claim 9, further comprising:
    generating an updated dose amount of the medication based on the extracted patient attributes and a predetermined regimen dose associated with the medication; and
    providing the updated dose amount and a visual illustration of a dose amount change in the overlay window.

11. The method of claim 8, wherein
    the extracted patient attributes include a patient weight or patient body surface area, and
    the one or more thresholds identify an upper limit or lower limit associated with a dose amount of the medication.

12. The method of claim 8, wherein the selection of the interactive icon comprises a mouse click or touchscreen input corresponding to the interactive icon.

13. The method of claim 8, wherein the selection of the interactive icon comprises a determination that a pointer location of a pointing device corresponds to a display location of the interactive icon.

14. The method of claim 8, wherein the operations further comprise:

applying a rule for rounding a dose amount of the medication;

displaying a rounded dose amount based on the applied rule; and displaying an interactive badge adjacent to the displayed rounded dose amount.

15. A non-transitory computer readable medium storing instructions which, when executed by at least one processor, cause the at least one processor to perform operations for generating dynamic multi-layered graphical user interfaces, the operations comprising:

retrieving, by the at least one processor from at least one networked database, treatment regimen data for a patient;

retrieving, by the at least one processor from the at least one networked database, patient attribute data for the patient, wherein the treatment regimen data identifies a dose of a medication determined based on a historical measurement of the patient in the patient attribute data;

generating, by the at least one processor, a graphical user interface reflecting the dose of the medication identified in the treatment regimen data and one or more associated patient attributes, wherein the associated patent attributes are extracted from the patient attribute data and reflect a current measurement of the patient;

comparing, by the at least one processor, the extracted patient attributes to one or more thresholds in a rule set, the rule set correlating the dose of the medication to one or more expected values of the extracted patient attributes;

evaluating, by the at least one processor based on the comparison, at least one condition of at least one rule in the rule set;

generating, by the at least one processor based on the evaluation, an interactive icon for display in the graphical user interface; and generating, by the at least one processor responsive to a selection of the interactive icon, an overlay window displayed adjacent the interactive icon, the overlay window providing details associated with the interactive icon.

16. The non-transitory computer readable medium of claim 15, wherein the interactive icon is associated with a recommendation to recalculate a dose of the medication.

17. The non-transitory computer readable medium of claim 16, the operations further comprising:

generating an updated dose amount of the medication based on the extracted patient attributes and a predetermined regimen dose associated with the medication; and providing the updated dose amount and a visual illustration of a dose amount change in the overlay window.

18. The non-transitory computer readable medium of claim 15, wherein the extracted patient attributes include a patient weight or patient body surface area, and the one or more thresholds identify an upper limit or lower limit associated with a dose amount of the medication.

19. The non-transitory computer readable medium of claim 15, wherein the selection of the interactive icon comprises one or more of a determination that a pointer location of a pointing device corresponds to a display location of the interactive icon, or a mouse click or touchscreen input corresponding to the interactive icon.

20. The non-transitory computer readable medium of claim 15, wherein the operations further comprise:

applying a rule for rounding a dose amount of the medication;

displaying a rounded dose amount based on the applied rule; and displaying an interactive badge adjacent to the displayed rounded dose amount.

* * * * *